United States Patent [19]

Barra et al.

[11] Patent Number: 5,554,736
[45] Date of Patent: Sep. 10, 1996

[54] AZO DYES CONTAINING A 2-(ARYLSULPHONYLAMINO)PYRIMIDINE RADICAL

[76] Inventors: Jordi B. Barra, c/Narcis Monturiol 64, 1.3., El Prat de Llobregat/Barcelona; Jose R. Sorolla, Avenida Carrilet 121, 4.1., L'Hospitalet de Llobregat/Barcelona, both of Spain

[21] Appl. No.: 471,432

[22] Filed: Jun. 6, 1995

Related U.S. Application Data

[62] Division of Ser. No. 430,794, Apr. 28, 1995, which is a continuation of Ser. No. 212,087, Mar. 14, 1994, abandoned.

[30] Foreign Application Priority Data

Mar. 16, 1993 [GB] United Kingdom ............... 9305374

[51] Int. Cl.⁶ .................... C09B 31/16; C09B 31/02; D06P 1/39; D06P 3/32
[52] U.S. Cl. ............... 534/755; 534/740; 534/757; 8/437; 8/639
[58] Field of Search .................. 534/740, 755, 534/757; 8/437, 639

[56] References Cited

U.S. PATENT DOCUMENTS

| | | | |
|---|---|---|---|
| 1,606,209 | 11/1926 | Montmollin et al. | 534/707 |
| 2,430,439 | 11/1947 | Stanley et al. | 544/297 |
| 2,746,951 | 5/1956 | Taube et al. | 534/707 X |
| 3,102,111 | 8/1963 | Csermely et al. | 534/794 |
| 4,962,191 | 10/1990 | Puntener et al. | 534/707 |

FOREIGN PATENT DOCUMENTS

| | | | |
|---|---|---|---|
| 1085987 | 7/1960 | Germany | 534/707 |

*Primary Examiner*—Fiona T. Powers
*Attorney, Agent, or Firm*—Robert S. Honor; Carl W. Battle; Carol A. Loeschorn

[57] ABSTRACT

The invention provides a process for the production of azodyes and their derivatives by diazotization and coupling reactions and optionally further modification reactions, wherein a compound of formula

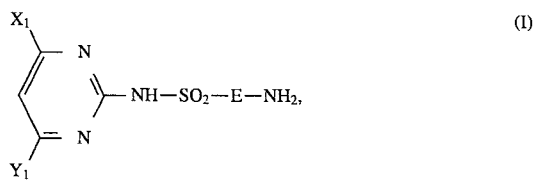

in which
E signifies an aromatic bivalent radical,
$X_1$ signifies hydroxy or a primary amino group,
$Y_1$ signifies hydroxy or a primary amino group
and in which the aminogroup linked to the —$SO_2$-bound phenyl radical may optionally be acylated,
or a mixture of compounds of formula (I), is employed as a coupling component or/and—in the non-acylated form—as a diazo component,
the invention in particular relates also to the novel dyes and their use and to the novel intermediates.

10 Claims, No Drawings

AZO DYES CONTAINING A 2-(ARYLSULPHONYLAMINO)PYRIMIDINE RADICAL

This is a division of application Ser. No. 08/430,794, filed Apr. 28, 1995, which in turn is a continuation of application Ser. No. 08/212,087, filed Mar. 14, 1994, now abandoned.

It has been found that particular 2-(arylsulphonylamino)-pyrimidine compounds are surprisingly well suitable as coupling and/or diazo components in the production of azo dyes and their derivatives, especially if they are used as middle components for the production of disazodyes and also higher polyazodyes and their derivatives, particularly metal complexes. There may be obtained dyes with valuable properties, especially for the dyeing of substrates dyeable with anionic dyes, in particular for leather and pelts.

The invention relates to the use of the defined pyrimidine compound as a coupling or/and diazo component in the production of azodyes and their derivatives, to the novel dyes, their production and use, and to the novel intermediates and their production.

The invention thus provides a process for the production of azodyes and their derivatives by diazotization and coupling reactions and optionally further modification reactions, wherein a component (M), which is a compound of formula

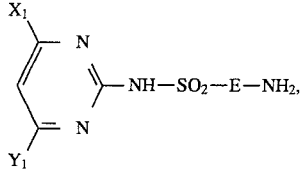

in which

E signifies an aromatic bivalent radical, $X_1$ signifies hydroxy or a primary amino group and $Y_1$ signifies hydroxy or a primary amino group, and in which the aminogroup linked to the —SO$_2$-bound radical E may optionally be acylated, or a mixture of compounds of formula (I), is employed as a coupling component or/and—in the non-acylated form—as a diazo component.

Preferably E is an aromatic carbocyclic radical that may contain one or more, preferably one or two, aromatic rings which may be further substituted. The substituents and their positions at these aromatic rings in E are preferably such that any coupling of a diazocompound takes place, at least preferentially, at the 5-position of the pyrimidine ring in formula (I), in which the E-bound group —NH$_2$ is optionally acylated.

Advantageously E is a phenylene radical that may be further substituted (e.g. with $C_{1-4}$-alkyl, $C_{1-4}$-alkoxy or/and chlorine) or a naphthylene radical, which is preferably further unsubstituted. If E signifies naphthylene the —SO$_2$-group is preferably in its 1-position and the optionally acylated —NH$_2$ group is preferably in the position 3 or 4.

Preferred compounds of formula (I) correspond to the following formulae:

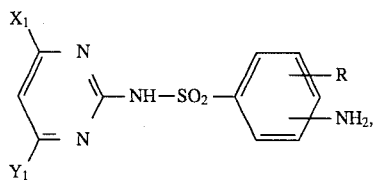

and

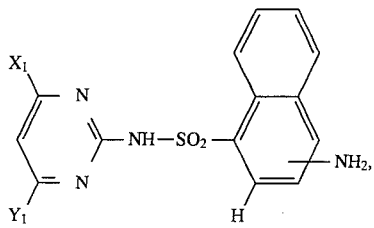

in which R signifies hydrogen or methyl, and in which the aminogroup linked to the —SO$_2$-bound phenyl or naphthyl radical may optionally be acylated, or mixtures thereof.

The —H in position ortho to —SO$_2$— in formula (I") indicates that this position is unsubstituted.

Among the above formulae (I') and (I") those of formula (I') are preferred.

The symbol R preferably signifies hydrogen.

The amino group linked to the —SO$_2$-bound aryl (preferably phenyl or naphthyl) radical is advantageously in one of the positions meta or para to the —SO$_2$-group; if this amino group is acylated it is preferably acylated with a protecting acyl group Ac that can, if required, easily be selectively hydrolyzed to the primary amino group. This Ac preferably is the acyl radical of a $C_{2-4}$-alkanoic acid, in particular acetyl. More preferably the amino group linked to the —SO$_2$-bound aryl radical E is not acylated.

$X_1$ preferably signifies OH.

Preferably component (M) is used as a coupling component, in which coupling takes place in the 5-position of the pyrimidine ring, and may - if the amino group linked to the —SO$_2$-bound aryl radical is not acylated - optionally be further diazotized and coupled.

For the production of azodyes preferably the diazocompound of a diazotizable amine or a mixture thereof is coupled to a component (M). If desired the obtained azo compound may be further reacted; in particular the primary amino group linked to the —SO$_2$-bound aryl radical E may be further diazotized and coupled to any coupling component, or the diazonium group may be hydrolyzed to OH; optionally this hydroxy group or/and a hydroxy group $X_1$ or $Y_1$ may be alkylated or the primary amino group linked to the —SO$_2$-bound aryl radical E or/and any primary amino group $X_1$ or $Y_1$ may by alkylated or acylated or further reacted, or/and a resulting metallizable azo compound may be metallized to corresponding metal complexes.

The invention thus provides in particular also a compound of formula

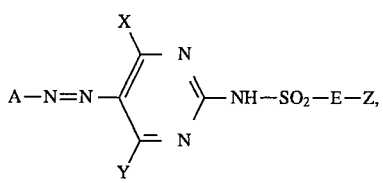
(II)

wherein

A signifies the radical of a diazo component or its modified derivative,

X signifies $X_1$, defined as above, or X',

Y signifies $Y_1$, defined as above, or Y',

X' signifies $C_{1-4}$-alkoxy, a mono- or di-($C_{1-4}$-alkyl)-amino group, an acylamino group or a carboxymethylamino group, Y' signifies $C_{1-4}$-alkoxy, a mono- or di-($C_{1-4}$-alkyl)-amino group, an acylamino group or a carboxymethylamino group, Z signifies a primary amino group —$NH_2$ or $Z_1$, $Z_1$ signifies hydroxy, $C_{1-4}$-alkoxy, a mono- or di-($C_{1-4}$-alkyl)-amino group, an acylamino group, a carboxymethylamino group or a group —N=N—B and B signifies the radical of a coupling component, or a mixture of compounds of formula (II), especially a compound of formula

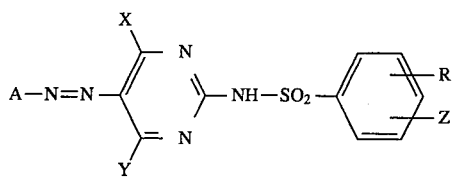
(II')

or of formula

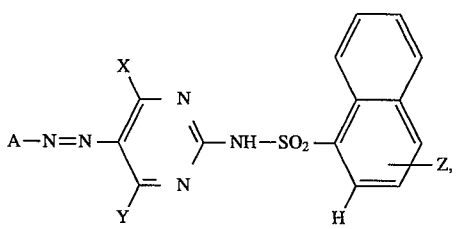
(II")

or a mixture of two or more compounds of formula (II') or/and (II").

Among the compounds of formulae (II') and (II") those of formula (II') are preferred.

Preferred dyes of formula (II) are those in which Z signifies —N=N—B, and which correspond to formula

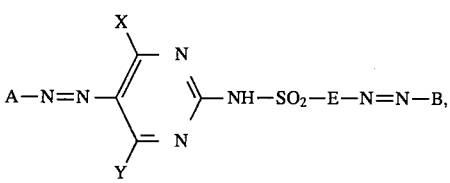
(IIa)

in particular to formula

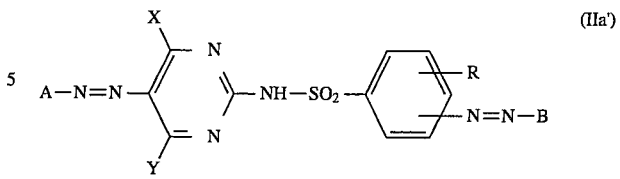
(IIa')

or to formula

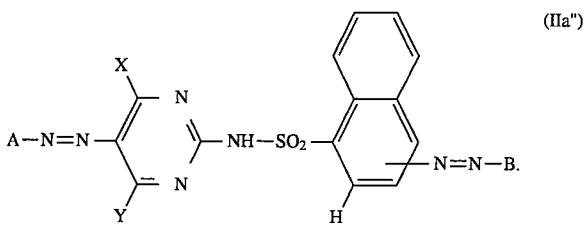
(IIa")

The process for the production of the compounds of formula (II) or mixtures thereof is in particular characterized in that the diazocompound of a di-azotizable amine or a mixture thereof is coupled to a component (M) and the primary amino group in the position of Z is optionally converted to $Z_1$ and $X_1$ or/and $Y_1$ is optionally converted to X' or/and Y'.

The $C_{1-4}$-alkyl radicals in the significances of X, Y and/or Z may be any such radicals as can be introduced by means of alkylation reactions of the respective hydroxy or primary amino groups, preferably ethyl or methyl. The acyl groups in the significances of X, Y and/or Z may be any such radicals as can be introduced by acylation reactions with conventional acylating agents, in particular the radicals of carboxylic or sulphonic acids, preferably of low molecular aliphatic carboxylic acids as suitable as protecting groups, in particular the acyl radicals of aliphatic monocarboxylic acids with 2 to 4, preferably 2 or 3 carbon atoms (principally acetyl or propionyl), or of lower aromatic sulphonic acids such as benzenesulphonyl or tosyl. Most preferably X and Y signify $X_1$ and $Y_1$ and Z preferably signifies —N=N—B.

The symbol A may signify the radical of any diazo component suitable for the production of azo dyes, or a modified derivative thereof. In particular A may signify the radical A' of a diazo component that may optionally contain a further azo group, particularly as deriving from diazotization of an amine of formula A'—$NH_2$, or a group of formula —A"—N=N—B which in particular derives from the diazotization of an amine of formula $Y_o$—A"—$NH_2$ (if A' signifies $Y_o$—A"—), wherein $Y_o$ signifies —$NO_2$ or —NH-Ac and Ac signifies a protecting aliphatic acyl group, coupling to a component (M) and, upon conversion of $Y_o$ to —$NH_2$, diazotizing and coupling to H—B. The radical A may also be the radical of a component derived from the bisdiazotization of a diamine of formula $H_2N$—A"—$NH_2$ and coupling of both diazonium groups to compounds of formula (I) to give the respective disazo or higher polyazo compounds. Where A' contains one or more azo groups these may e.g. derive from previous diazotization and coupling reactions and optionally other suitable reactions (such as the hydrolysis of an acylated amino group or the reduction of a nitro group to give a primary amino group) to give—as A'—$NH_2$—an azo group-containing compound that contains a diazotizable primary amino-group.

Preferably A is A', and A' preferably is the radical of a diazo component of the benzene or/and naphthalene series containing 1 to 4 aromatic rings and which, if it contains 2 to 4 aromatic rings, may contain a heteroatomic bridge between two aromatic rings.

The heteroatomic bridge between two aromatic cycles in A' or A" is preferably a nitrogen-containing bridge, especially an azo group, an imino bridge or an amido bridge (e.g. carbonylamino or sulphonylamino); the aromatic rings in A' and A" may be substituted with substituents conventional in diazo components in azo-dyes, especially in anionic (poly)azo dyes.

Suitable amines A'—$NH_2$ are, in particular, those of the following formulae

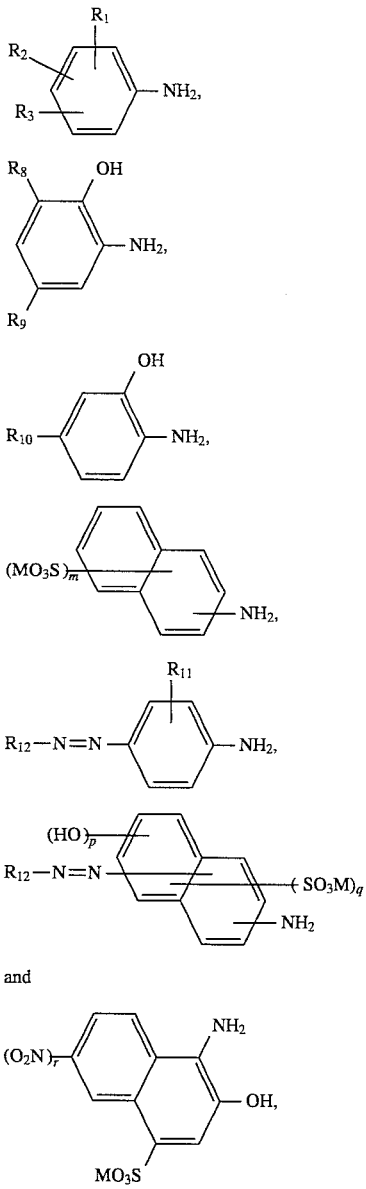

wherein $R_1$ signifies hydrogen, nitril, trifluoromethyl, nitro, —$SO_3M$, —$SO_2NR_4R_5$, —COOM or —$CONR_4R_5$, $R_2$ signifies hydrogen, nitro, —$SO_3M$, —$SO_2NR_4R_5$, trifluoromethyl, nitril, —COOM, —$CONR_4R_5$, $C_{1-4}$-alkyl, $C_{1-4}$-alkoxy, halogen or $C_{1-2}$-mercaptoalkyl, $R_3$ signifies hydrogen, $C_{1-4}$-alkyl, $C_{1-4}$-alkoxy, halogen, $C_{1-2}$-mercaptoalkyl, —NH-Ac, —NH—CO—O—$CH_3$ or a radical of formula

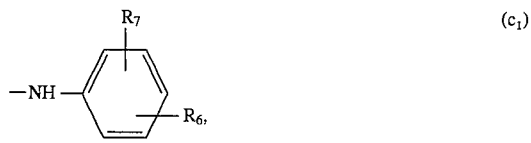

$R_4$ signifies hydrogen, $C_{1-4}$-alkyl, $C_{1-4}$-alkylene-R' or $C_{2-3}$-hydroxyalkyl, $R_5$ signifies hydrogen, $C_{1-4}$-alkyl, $C_{1-3}$-alkylene-R', $C_{2-3}$-hydroxyalkyl, benzyl or a radical of formula R' signifies nitril, carbamoyl or —COOM, $R_6$ signifies hydrogen, nitro or —$SO_3M$, $R_7$ signifies hydrogen, methyl, chlorine, nitro, —COOM or —$SO_3M$, $R_8$ signifies hydrogen, halogen, nitro, —$SO_3M$, —$SO_2NR_4R_5$, methylsulphonyl, $C_{1-4}$-alkyl or —NH-Ac, $R_9$ signifies hydrogen, halogen, nitro, —$SO_3M$, —$SO_2NR_4R_5$, methylsulphonyl, $C_{1-4}$-alkyl or —NH-Ac, $R_{10}$ signifies nitro, —$SO_3M$ or —$SO_2NR_4R_5$, $R_{11}$ signifies hydrogen, $C_{1-4}$-alkyl, $C_{1-4}$-alkoxy, hydroxy, —$NH_2$ or —NH-Ac, $R_{12}$ signifies the radical of a diazo component deriving from the diazotization of an amine of formula ($a_1$), ($a_2$), ($a_3$), ($a_4$) or ($a_7$), Ac signifies an aliphatic acyl group, m signifies 0 or 1, P signifies 0 or 1, q signifies 0, 1 or 2 and r signifies 0 or 1.

Suitable amines of formula $Y_o$—A"—$NH_2$ are those of formula A'—$NH_2$ that contain a substituent $Y_o$, in particular of formula ($a_1$), ($a_2$), ($a_3$) or ($a_7$) containing a nitro group or of formula ($a_1$), ($a_2$), ($a_5$) or ($a_7$) containing a group —NH-Ac.

$R_1$ preferably signifies hydrogen or —COOM.

Of the alkyl and alkoxy groups with 1 to 4 carbon atoms, the lower molecular weight ones are preferred, in particular ethyl, methyl, ethoxy and methoxy. Halogen may in particular be fluorine, chlorine or bromine of which fluorine and, before all, chlorine are preferred.

Where in formula ($a_1$) $R_3$ signifies a radical of formula ($c_1$) this is preferably in para-position to the amino group, $R_1$ preferably signifies hydrogen, $R_2$ preferably signifies hydrogen or a sulpho group and, if $R_2$ signifies a sulpho group, this is preferably in meta-position to the azo group and $R_6$ and $R_7$ preferably signify both hydrogen or, if $R_2$ signifies hydrogen, $R_6$ signifies preferably a nitro group and $R_7$ signifies preferably a carboxy group or a sulpho group, the two substituents $R_6$ and $R_7$ being placed in the para-position to the imino group and in one of the two orthopositions to the imino group.

Where the symbol $R_3$ does not signify a radical ($c_1$), $R_3$ preferably signifies hydrogen and $R_1$ preferably signifies hydrogen or —COOM. According to a preferred feature, in this case in formula ($a_1$) one or both of the positions ortho to the primary amino group and, more preferably, also one or both of the positions meta to the primary amino group are unsubstituted. According to a further preferred feature, if $R_1$ signifies —COOM, this is in position ortho to the diazotizable primary amino group.

$R_4$ preferably signifies hydrogen.

$R_5$ advantageously signifies hydrogen, methyl, ethyl, hydroxyethyl or a radical of formula ($c_2$), in which $R_7$ preferably signifies hydrogen or carboxy.

The aliphatic acyl group Ac advantageously signifies the radical of a low molecular weight aliphatic carboxylic acid, preferably of an alkanoic acid with 2 to 4 carbon atoms, more preferably acetyl or propionyl, of which acetyl is preferred.

In formula ($a_2$) preferably at least one of $R_8$ and $R_9$ has a significance other than hydrogen, more preferably $R_9$ has a significance other than hydrogen and $R_8$ signifies hydrogen, a nitro group of a sulpho group.

The primary amino group in formula ($a_4$) may be in any of the positions α and β of the naphthalene ring and, if m signifies 1, the sulpho group may be in any of the other available positions, preferably so that at least one vicinal position to the amino group is unsubstituted; e.g. if the amino group is in position 1, the sulpho group is preferably in any of the positions 3 to 8, more preferably 4 to 8, and if the amino group is in the position 2, the sulpho group is e.g. in position 1 or in any of the positions 4 to 8, more preferably 5, 6 or 7.

If in formula ($a_5$) $R_{11}$ signifies —OH, —NH$_2$ or —NHAc it is preferably in position meta to the group —NH$_2$; preferably the symbol $R_{11}$ signifies hydrogen.

In the significance of $R_{12}$ are preferred the diazo components of the benzene series, in particular those of formula ($a_1$), ($a_2$) and ($a_3$).

In formula ($a_6$) the primary amino group may be in any of the positions α and β of the naphthalene nucleus; if q is 1 or 2, the respective sulpho groups may be in any of the available other positions. If p=0, q preferably signifies 1 and the respective sulpho group is preferably in one of the positions 4 to 8, with respect to the primary amino group being in one of the positions 1 and 2. If p=0 more preferably the amino group is in position 1 and the azo group in position 4, any q sulpho groups preferably being in any of the positions 5 to 8. If p=1 the hydroxy group and the amino group are preferably in the positions 1,8 and q is preferably 1 or 2, the q sulpho groups being more preferably located in q of the positions 3 to 6; the group $R_{12}$—N=N— is preferably in a position ortho or para to the hydroxy group. Also in formula ($a_6$) $R_{12}$ is preferably the radical of a diazo component of the benzene series, in particular of formula ($a_1$), ($a_2$) or ($a_3$).

The compounds ($a_7$) are indicated in the free amine form, as diazo components they are however usually employed directly in the form of the respective commercially available diazonium compounds 1-diazonium-2-naphthol-4-sulphonic acid (in which r=0) and 1-diazonium-6-nitro-2-naphthol-4-sulphonic acid (in which r=1).

Preferably A, in particular A' and A", contains at least one hydrophilic substituent, preferably a substituent selected from the group consisting of —SO$_3$M, —SO$_2$NR$_4$R$_5$, —COOM and —CONR$_4$R$_5$, more preferably not more than one hydrophilic substituent per homocyclic aromatic nucleus.

B signifies the radical of a coupling component H—B, which may be any coupling component, in particular of the benzene, naphthalene, heterocyclic or open-chain methylene-active series, and suitably contains at least one substituent that activates the compound H—B for coupling; in particular an aromatically bound or enolic, optionally etherified hydroxy group or an optionally substituted amino group, so that the coupling reaction may take place in the corresponding activated position of the molecule H—B.

Suitable coupling components H—B are, in particular, those of the following formulae

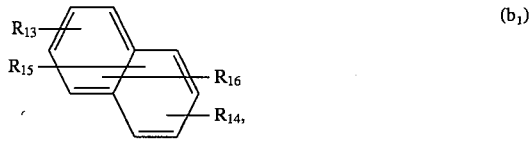
(b$_1$)

(b$_2$)

(b$_3$)

(b$_4$)

(b$_5$)

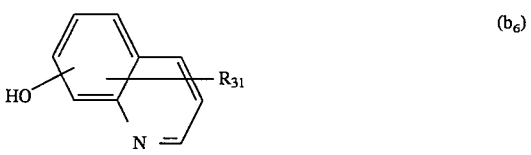
(b$_6$)

and $$R_{32}-G-CO-CH_2-CO-R_{33}, \quad (b_7)$$

wherein $R_{13}$ signifies hydrogen, —OR$_{17}$ or —NHR$_{17}$, $R_{14}$ signifies —OR$_{17}$ or —NHR$_{17}$, $R_{15}$ signifies hydrogen, —SO$_3$M, —SO$_2$NR$_4$R$_5$, —COOM or —CONR$_4$R$_5$, $R_{16}$ signifies hydrogen, —SO$_3$M, —SO$_2$NR$_4$R$_5$, —COOM or —CONR$_4$R$_5$, $R_{17}$ signifies hydrogen, $C_{1-4}$-alkyl, Ac' or a radical of formula

(c$_3$)

Ac' signifies the acyl radical of an aliphatic carboxylic acid,

Q signifies —CO—, —SO$_2$— or the direct bond, $R_{18}$ signifies hydrogen, methyl, —NH-Ac, —COOM or —NO$_2$ or, if in formula (c$_3$) Q signifies —CO— or —SO$_2$—, also —NH$_2$, $R_{19}$ signifies —OH or —NH$_2$, $R_{20}$ signifies hydrogen, $C_{1-4}$-alkyl, $C_{1-4}$-alkoxy, —OH, —NR"R'" or —NH-Ac, $R_{21}$ signifies hydrogen, $C_{1-4}$-alkyl or $C_{1-4}$-alkoxy, R" and R'" independently, signify hydrogen, $C_{1-2}$-alkyl or $C_{2-3}$-hydroxyalkyl, $R_{22}$ signifies hydrogen, sulphonaphthyl or a radical of formula

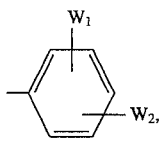  (c$_4$)

$W_1$ signifies hydrogen, halogen, methyl, methoxy or —COOM, $W_2$ signifies hydrogen, halogen, trifluoromethyl, nitril, nitro, —COOM, —SO$_3$M or —SO$_2$NR$_4$R$_5$, $R_{23}$ signifies $C_{1-4}$-alkyl, phenyl, —COOM, —CONR$_4$R$_5$, —COOCH$_3$ or —COOC$_2$H$_5$, $R_{24}$ signifies =O or =NH, $R_{25}$ signifies hydrogen, unsubstituted amino, phenylamino, sulphonaphthyl, open-chain $C_{1-8}$-alkyl, $C_{6-9}$-cycloalkyl, carboxy-($C_{1-4}$-alkyl), $C_{2-4}$-alkyl substituted with hydroxy, methoxy, ethoxy or a sulpho group in one of the positions β to ω, or a radical of formula (c$_4$), $R_{26}$ signifies hydrogen, nitril, acetyl, —COOM, carbamoyl, —SO$_3$M, pyridinio or 2-methyl-pyridinio, $R_{27}$ signifies hydrogen, hydroxy, methyl, carboxy, phenyl, sulphomethyl or carbamoyl, $R_{28}$ signifies hydroxy, primary amino, nitrilamino, thiol or a radical of formula

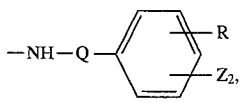  (c$_5$)

$R_{29}$ signifies hydroxy or primary amino, $R_{30}$ signifies hydroxy or primary amino, $R_{31}$ signifies hydrogen, methyl, chlorine, chloromethyl or chloroacetyl, G signifies —O—, —NH— or the direct bond, $R_{32}$ signifies naphthyl, sulphonaphthyl, disulphonaphthyl or a radical of formula (c$_4$), $R_{33}$ signifies $C_{1-4}$-alkyl, $Z_2$ has a significance of Z, which is preferably other than —N=N—B, and, where in formula (b$_4$) $R_{26}$ stands for pyridinio or orthomethylpyridinio, any of the sulpho groups present in the molecule may be in the form of the anion —SO$_-$ to form the counterion in the form of the inner salt, or a further compound of formula (I).

The aliphatic acyl radical Ac' in the significance of $R_{17}$ may be the radical of any aliphatic carboxylic acid as can be introduced by acylation, in particular of a $C_{2-12}$-alkanoic primary monocarboxylic acid, preferably such as stated above for Ac, especially $C_{2-4}$-alkanoyl, most preferably acetyl.

If $R_{18}$ signifies —COOM, Q in formula (c$_3$) signifies in particular —CO—. If in formula (c$_3$) Q signifies the direct bond, $R_{18}$ preferably signifies hydrogen. If in formula (c$_3$) Q signifies —SO$_2$—, $R_{18}$ preferably signifies methyl, acetylamino or —NH$_2$. If in formula (c$_3$) Q signifies —CO—, $R_{18}$ preferably signifies hydrogen or $_{NO2}$.

In formula (b$_1$) —OR$_{17}$ preferably signifies hydroxy and —NHR$_{17}$ preferably signifies —NHR$_{17}$', where $R_{17}$' signifies hydrogen, methyl, acetyl or a radical of formula (c$_3$). Preferably $R_{14}$ signifies hydroxy or —NHR$_{17}$' and $R_{13}$ signifies hydrogen or, where $R_{14}$ signifies —OH, also a group —NHR$_{17}$'. More preferably either $R_{14}$ signifies hydroxy and $R_{13}$ signifies hydrogen or —NHR$_{17}$' or $R_{14}$ signifies —NHR$_{17}$' and $R_{13}$ signifies hydrogen. $R_{15}$ preferably signifies hydrogen, —SO$_3$M, —COOM or —CONH$_2$. $R_{16}$ preferably signifies hydrogen or —SO$_3$M, more preferably hydrogen.

If in formula (b$_2$) $R_{20}$ signifies hydroxy, —NR"R'" or —NH-Ac, it is preferably in meta-position to $R_{19}$ and $R_{21}$ preferably signifies hydrogen. If $R_{20}$ signifies $C_{1-4}$-alkyl or $C_{1-4}$-alkoxy it may be in any of the available positions ortho, meta and para to $R_{19}$. More preferably $R_{19}$ signifies hydroxy. Advantageously $R_{21}$ signifies hydrogen.

Of the alkyl and alkoxy radicals with 1 to 4 carbon atoms, also in B the lower molecular weight ones are preferred (analogously as in A), more specifically ethyl, methyl, ethoxy and methoxy. In the $C_{2-3}$-hydroxyalkyl radicals the hydroxy group is preferably in β-position.

In formula (b$_3$) $R_{22}$ preferably signifies a radical of formula (c$_4$). In formula (c$_4$)—in the significance of $R_{22}$—preferably at least one of $W_1$ and $W_2$ signifies hydrogen, more preferably $W_1$. $R_{23}$ preferably signifies $C_{1-4}$-alkyl, more preferably methyl. $R_{24}$ preferably signifies oxygen.

The open-chain $C_{3-8}$-alkyl radicals in the significance of $R_{25}$ may be linear or branched, if they contain 6 to 8 carbon atoms they are preferably branched; the cycloalkyl radicals in the significance of $R_{25}$ are preferably cyclohexyl, which may be substituted with 1 to 3 methyl groups, more preferably it is unsubstituted cyclohexyl. The carboxy-substituted $C_{1-4}$-alkyl group preferably is carboxymethyl or β-carboxyethyl. The substituent (hydroxy, methoxy, ethoxy, sulpho) at the $C_{2-4}$-alkyl, in the significance of $R_{25}$, is preferably in β-position. If $R_{25}$ signifies a radical of formula (c$_4$) $W_1$ preferably signifies hydrogen and $W_2$ preferably signifies carboxy, sulpho or trifluoromethyl. Preferred significances of $R_{25}$ are hydrogen, a radical of formula (c$_4$), $C_{1-8}$-alkyl, $C_{2-3}$-hydroxyalkyl and $C_{6-9}$-cycloalkyl.

$R_{26}$ preferably signifies hydrogen, a sulpho group or one of the stated nitrogen-containing substituents.

$R_{27}$ preferably has a significance other than hydrogen, more preferably methyl.

In formula (b$_5$) preferably at least one of $R_{29}$ and $R_{30}$ signifies hydroxy, more preferably both $R_{29}$ and $R_{30}$ signify hydroxy groups.

If in formula (b$_5$) $R_{28}$ signifies a radical of formula (c$_5$), —NH—Q— preferably signifies a group —NH—SO$_2$—.

In formula (b$_6$) the hydroxy group preferably is in position 8. If $R_{31}$ is other than hydrogen it is preferably in position para to the 8-positioned hydroxy group. $R_{31}$ preferably signifies hydrogen or methyl, more preferably hydrogen.

In formula (b$_7$) G preferably signifies —NH—. More preferably $R_{32}$ or unsubstituted phenyl and $R_{33}$ is preferably methyl.

The coupling component radical B preferably contains up to three cycles (homocyclic rings, heterocyclic rings and optionally a cycloaliphatic ring—a naphthalene radical being calculated as two cycles), more preferably B contains one or two of such cycles.

Of the above dyes of formula (II) are preferred those dyes in which Z signifies —N=N—B, especially those in which A and B together contain 2 to 6, especially 2 to 4 cycles and one or two hydrophilic groups, the hydrophilic groups for A' and A″ being as indicated above and for B being as indicated above for A′ or A″ or also a cationic group, in particular a pyridinium or orthomethylpyridinium group as stated in the significances of $R_{26}$ if B is the radical of a coupling component of formula ($b_4$).

The compounds of formula (I) are in part known. Those in which $X_1$ and $Y_1$ signify —$NH_2$ and those in which E signifies a naphthylene radical constitute also part of the invention. The compounds of formula (I) can be produced in a manner known per se, in particular by reacting a guanide of formula $$HN=C(NH_2)-NH-SO_2-E-NH_2, \quad (\alpha)$$

in particular of formula

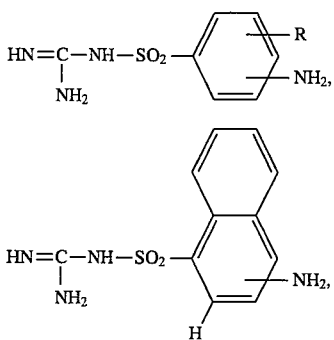

in which the aromatically bound amino group is optionally acylated with Ac, with a compound of formula $$Z'-CH_2-Z'' \quad (\beta),$$

in which

Z′ signifies —CN or —CO—($C_{1-2}$-alkyl)
and

Z″ signifies —CN or —CO—($C_{1-2}$-alkyl),
under cyclizing reaction conditions.

This reaction is carried out expediently in the presence of an akali metal alcoholate, preferably sodium methanolate, ethanolate or isopropanolate, optionally in the presence of alcohol (but suitably in the absence of water or other protogenic solvents that might react preferentially with the alkali metal alcoholate), with heating, preferably at temperatures >60° C. more preferably under reflux.

If desired, in the cyclization product a primary amino group linked to the aromatic radical E may be acylated in a manner conventional per se, preferably with Ac.

The compounds of formula (α) can be produced in a manner conventional per se, in particular by amidation of guanidine with the respective sulphonic acid halide, in particular chloride or bromide, of formula $$Hal-SO_2-E-NHAc \quad (\gamma),$$

in particular

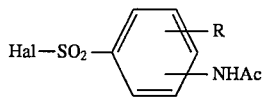

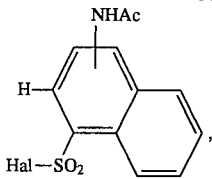

in which

Hal signifies halogen, preferably Br or Cl, and Ac is as defined above, and, if desired, splitting off any group Ac by selective hydrolysis.

Diazotization of amines of formula A′—$NH_2$ and of formula (II) in which Z signifies —$NH_2$, may be carried out under conventional conditions, in particular with a nitrite (preferably sodium nitrite) in acidic aqueous medium (preferably in the presence of hydrochloric acid) and at low temperatures, e.g. in the range of −5° C. to +10° C., preferably 0° to 5° C. The coupling reactions of the diazonium compounds to the respective coupling components may also be carried out in a manner conventional per se, advantageously at temperatures below 25° C., preferably in the range of 0° to 15° C., more preferably in the range of 0° to 10° C. The coupling of a diazo compound, e.g. of an amine of formula A′—$NH_2$, or of a mixture thereof, to a component (M) may be carried out under distinctly acidic to strongly basic pH conditions, e.g. at pH in the range of 4 to 13, preferably 9 to 11. The coupling of the diazo compound of an amine of formula (II), in which Z signifies —$NH_2$, or a mixture thereof, to the corresponding coupling components H—B may be carried out under distinctly acidic to strongly basic pH conditions, advantageously in the range of pH 4 to pH 12, in particular to coupling components of formula ($b_1$), ($b_2$), ($b_4$), ($b_5$), ($b_6$) or/and ($b_7$) preferably at pH values in the range of 9 to 11, and to coupling components of formula ($b_3$) preferably in the pH range of 5 to 11. The reactions may be carried out in aqeuous medium or also in aqueous/organic medium, the organic medium being preferably a water-miscible inert solvent-(e.g. an alcohol or dioxane). The acylation of the amino groups with an acid halide takes advantageously place in the presence of a dehydrohalogenating agent, in particular of an alkali metal hydroxide, and at temperatures suitably in the range of 15° to 50° C., preferably 20° to 40° C.

Where more than one coupling position is available, the coupling position may be influenced or determined by suitable selection of the pH value during the coupling reaction (stronger acidic pH-conditions favour e.g. coupling in ortho to an amino group).

According to a particular feature of the invention A contains a metallizable substituent in ortho position to the azo group bound to the pyrimidine ring and also X represents a substituent that is metallizable together with it. Such compounds are in particular compounds of formula (II) or mixtures thereof, wherein A signifies the radical of a diazo component HO—(CO)$_n$—$A_1$—$NH_2$, in which the substituent —(CO)$_n$—OH is in ortho position to the diazotizable amino group, —$A_1$— is the ortho-bivalent radical and n signifies 0 or 1,
or its modified derivative, X signifies $X_1$,
and Z is in position meta or para to —$SO_2$—, and which correspond to the formula

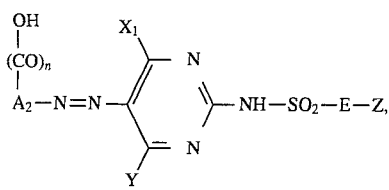 (III)

in particular

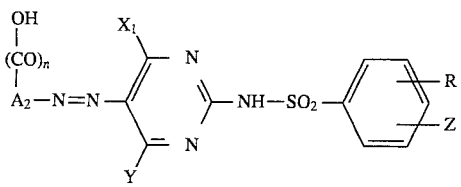 (III')

or

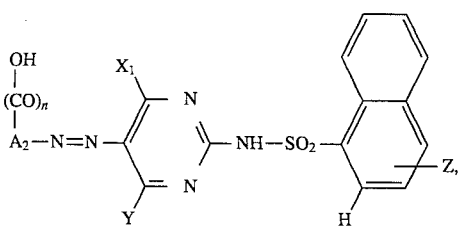 (III'')

wherein $A_2$ is an ortho-bivalent radical $A_1$ or its modified derivative.

As modified derivative in the definition of $A_2$ with respect to $A_1$ there is meant substantially the same as described above for A in respect to a radical of a diazo component, in particular in respect to A'.

Preferably HO—$(CO)_n$—$A_2$— is the radical of a diazo component HO—$(CO)_n$—$A_1$—$NH_2$, which is more preferably a diazo component of formula ($a_1$) with a carboxy group in ortho-position to —$NH_2$, of formula ($a_5$) in which $R_{11}$ signifies —OH in ortho-position to the diazotizable amino group, or of formula ($a_2$), ($a_3$) or ($a_7$).

These metallizable compounds may be directly used as dyes, as described in more detail below, or may be converted to the respective metal complexes by metallization with complex-forming metal compounds, optionally in combination with further complex-forming ligands H—Lg'—H, and optionally with further reactions, in particular to the repective metal complexes of formula

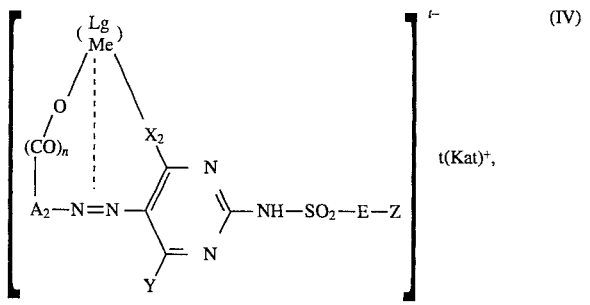 (IV)

preferably

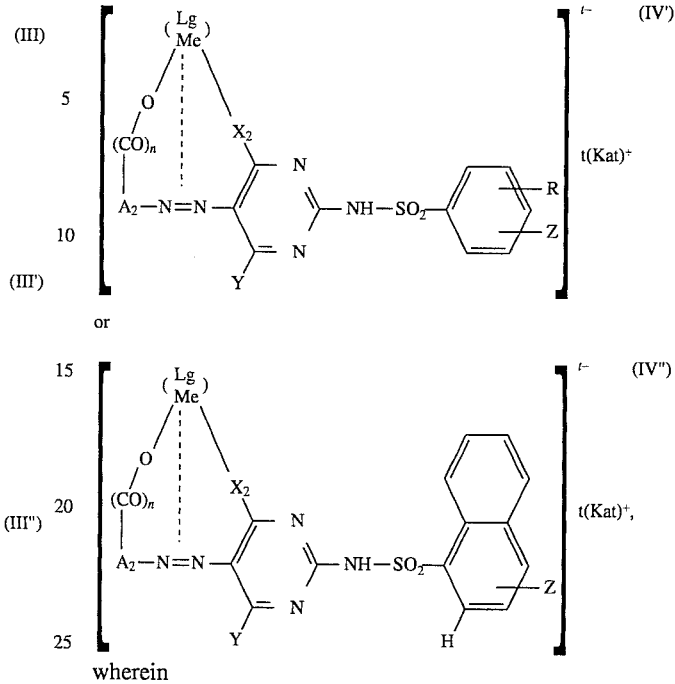

wherein
$X_2$ signifies —O— or —NH—,
Me signifies a complex-forming metal,
Lg signifies a ligand or a group of ligands,
t is the number of negative charges of the Me-complex
and $(Kat)^+$ signifies a counterion, viz. a cation,
or mixtures of two or more thereof.

The ligand H—Lg'—H may be any chromophoric or non-chromophoric ligand or group of ligands, e.g. non-chromophoric ligands such as molecules of coordinatively linked water, ammonia, aliphatic polyamines (e.g. ethylene diamine or diethylene triamine) or hydroxycarboxylic acids (e.g. tartaric or salicylic acid), or chromophoric ligands such as a molecule of a metallizable azo compound, e.g. of the kind HO—$(CO)_n$—$A_2$—N=N—B [where HO—$(CO)_n$—$A_2$— is e.g. the radical of a diazo component of formula HO—$(CO)_n$—$A_1$—$NH_2$ which is preferably of formula ($a_1$) with a carboxy group in ortho-position to —$NH_2$, of formula ($a_5$) with $R_{11}$ signifying hydroxy in ortho to the diazotizable amino group, or of formula ($a_2$), ($a_3$) or ($a_7$), while B contains a metallizable substituent in ortho to the coupling position] or of the kind HO—$(CO)_n$—$A_3$—N=N—B [where HO—$(CO)_n$—$A_3$— is the radical of a diazo component of formula HO—$(CO)_n$—$A_3$—$NH_2$ that contains a metallizable azo group and which is preferably of formula ($a_5$) or ($a_6$) that is metallizable at the azo group] or, according to a preferred feature, a further compound of formula (III), in particular (III'') or preferably (III').

The complex-forming metal may be any suitable metal, in particular chromium, cobalt, iron, copper, nickel, manganese, titanium, zirconium (also zirconyl) or/and aluminium, of which are preferred chromium, cobalt, iron, nickel and copper, before all the 1:2 complex-forming metals, especially chromium, cobalt and/or iron optionally in combination with minor proportions of aluminium.

The number t depends on Me, Lg and the compound of formula (III) and may in particular be 0, 1 or 2. If any of Lg, Z or/and $A_1$ contains a covalently bound cationic group, e.g. a pyridinium group as mentioned above, their positive charges may equilibrate, at least in part, a corresponding number of negative charges of the complex, so that t is reduced accordingly. It is however preferred that in the dye molecules of the invention the covalently bound anionic groups prevail. $(Kat)^+$ may be any cation as is formed in the synthesis of the respective dye and depends thus also on Lg and Me and further also on the complex-forming reaction conditions (namely the pH and the employed solvent), or a cation introduced by ion exchange; in the free acid form it is indicated as a hydroxonium ion.

Preferred metal complexes are those of compounds of formula (III), especially (III") or preferably (III'), in which Preferably the metal complexes are 1:2 complexes, especially those in which the complex-forming metal is iron, cobalt or chromium, among which cobalt and especially chromium are preferred.

A preferred group of metal complexes among these are metal complexes of the formula

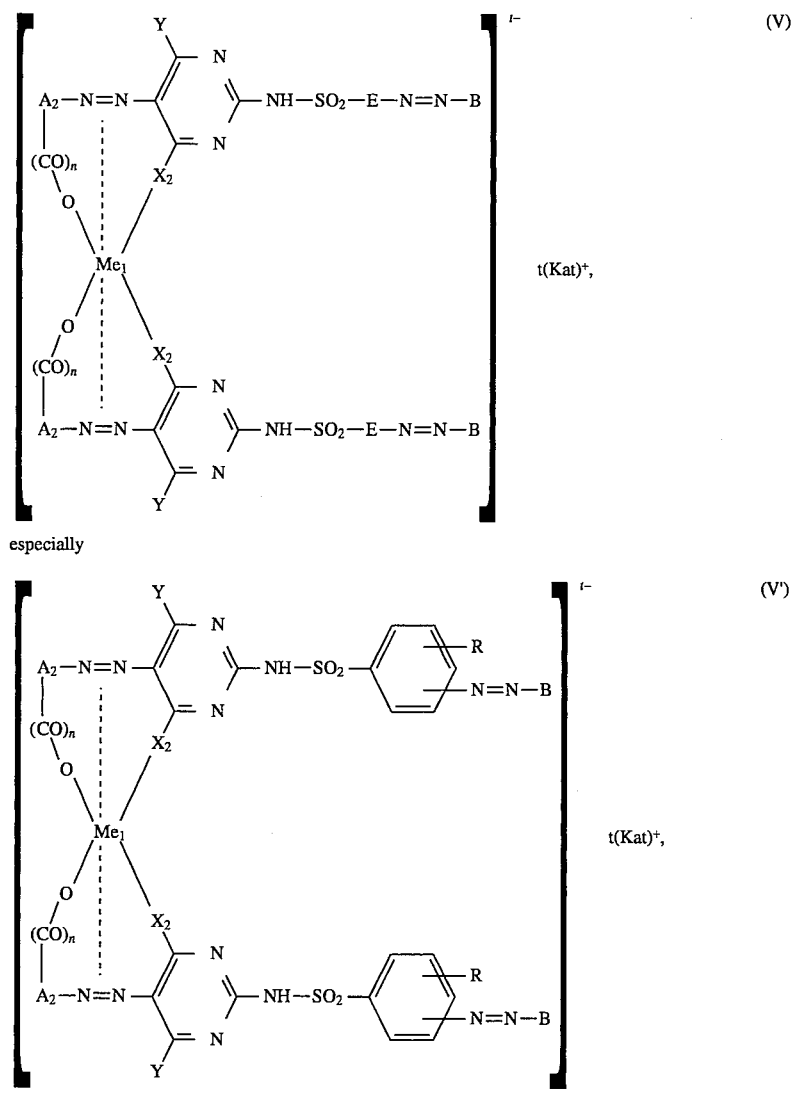

—$A_2$—$(CO)_n$—OH is the radical of a diazo component of the benzene or/and naphthalene series containing 1 to 4 aromatic rings and which, if it contains 2 to 4 aromatic rings, may contain a heteroatomic bridge between two aromatic rings, Z is a group —N═N—B, B is the radical of a coupling component of the benzene, naphthalene, heterocyclic or open-chain methylene-active series and the complex-forming metal is copper, nickel, iron, chromium or cobalt.

wherein $Me_1$ signifies iron, cobalt or chromium, or mixtures of such complexes.

The process for the production of the metal complexes or mixtures stated above is in particular characterized in that a) a metallizable compound of formula (III) [in particular (III') or/and (III")] or a mixture thereof and optionally one or more further complex-forming ligands are reacted with a complex-forming metal compound, or b) a metal complex compound of formula (IV) in which Z signifies —$NH_2$ and Y signifies $Y_1$, of the formula

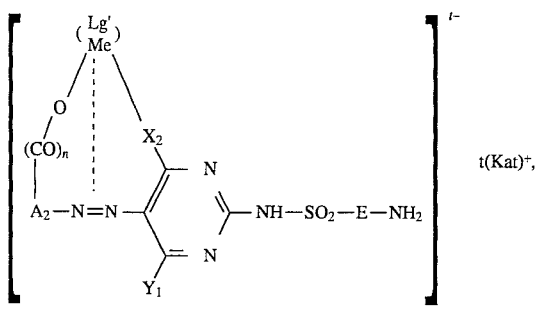

(VI)

in particular

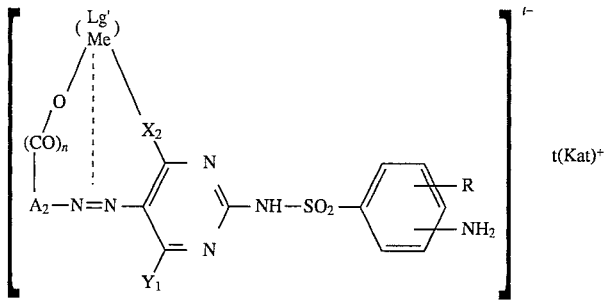

(VI')

or

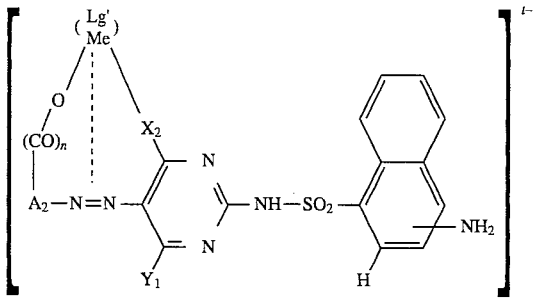

(VI")

wherein Lg' has a significance of Lg or is a ligand which, after conversion of —NH$_2$ to Z$_1$ and optionally of Y$_1$ to Y, leads to Lg,
or a mixture thereof, is converted to a metal complex of formula (IV) or mixture thereof, in which Z signifies Z$_1$.

The metallization to metal complexes may be carried out in analogy to known metal complex formation reactions.

For the metallization of the compounds of formula (III) there may be employed conventional suitable metal compounds e.g. acetates or hyrosoluble salts of mineral acids, in particular chromium trichloride, cobalt dichloride, copper dichloride or sulphate, iron di- or trichloride, chromium trifluoride, manganese chloride, acetate or sulphate, aluminium chloride, titanium chloride, zirconium tetrachloride or sulphate, zirconyl chloride, cobalt sulphate or nitrate, iron-II- or -III-sulphate, chromium sulphate, chromium or cobalt acetate, potassium chromium sulphate, ammonium chromium sulphate (e.g. chrome alums) and optionally, with the addition of a reducing agent e.g. of glucose, also sodium or potassium chromate or bichromate.

The chromation may be carried out directly up to the 1:2-chromium complex stage or by degrees over the 1:1-chromium complex stage and then further complexation up to the 1:2-chromium complex stage.

Chromation may be carried out in aqueous medium, preferably at pH values in the range of 2 to 10 and temperatures in the range of 95° to 130° C., if necessary under superatmospheric pressure. Optionally the reaction may be carried out with addition of organic solvents or also only in organic solvents. Suitable organic solvents are preferably such that are miscible with water, have a boiling point above 100° C. and in which the azo dyes and the metal salts are soluble, e.g. glycols, ether alcohols or amides (e.g. ethylene glycol, polyethylene glycols, β-ethoxyethanol, β-methoxyethanol, formamide or dimethylformamide). For the production of asymmetrical 1:2-chromium complex compounds the chromation may be carried out gradually, synthetizing first the 1:1-chromium complex of one of the complexants and from this with a second complexant than the 1:2-complex. The 1:1-chromium complexes may be produced in conventional manner, e.g. under analogous conditions as for the 1:2-chromium complexes, but preferably under stronger acidic pH-values, advantageously at pH<3. It is also of advantage to synthesize 1:2-chromium mixed complexes by simultaneously metallizing different complexants of formula (III) and H—Lg'—H or to couple the diazo compound of a compound of formula (VI) to one or more coupling components H—B.

Preference is given to 1:2-chromium complexes of symmetrical constitution, e.g. of formula (V) in which the two symbols A$_2$ have the same significance, the two symbols B have the same significance, the two symbols Y have the same significance, the two symbols E have the same significance and the two groups —N=N—B are in the same position (preferably para).

The metallization of azo compounds of formula (III) to the corresponding ironcomplexes, mainly 1:2-ironcomplexes, may be carried out in conventional manner, suitably in aqueous medium, advantageously at pH-values in the range of 3.5 to 6.5, preferably 4 to 6, with heating. Preferably the metallization to iron complexes is carried out at temperatures in the range of 40° C. to reflux temperature, preferably 60° to 100° C.

The metallization of azo compounds of formula (III) to the corresponding cobalt complexes, mainly 1:2-cobalt complexes, may be carried out in conventional manner, suitably in aqueous medium, advantageously at pH-values in the range of 9 to 12, preferably 10 to 11, optionally with heating. Preferably the metallization to cobalt complexes is carried out at temperatures in the range of 30° C. to 90° C., preferably 40° to 70° C.

The metallization to copper complexes is preferably carried out at pH 7 to 10 and at tempeatures in the range of 60° to 100° C., preferably with copper sulphate.

Other metallizations may be carried out in analogous way, as conventional per se.

Of the above process variants a) and b) process variant b) is preferred.

Upon completion of the required coupling and optionally metallization or/and further optional modification reactions the obtained dyes or mixture thereof may be isolated from the mother-lye in a manner conventional per se, e.g. by salting out or by acidification with a strong mineral acid or e.g. by evaporation, upon dialysis through a suitable membrane. If desired, the dye may, upon isolation or dialysis, be blended with suitable blending agents conventional per se, e.g. alkali metal salts (sodium carbonate, sodium sulphate) non-electrolyte blending agents (mainly oligosaccharides, e.g. dextrine) or/and with anionic surfactants, in particular hydrocarbon sulphonates, e.g. sulphonated castor oil, sulphosuccinates or lignine sulphonate. If a surfactant is employed the weight ratio of the surfactant to the dye is advantageously in the range of 5:95 to 40:60. If desired, especially if the composition contains an anionic surfactant, as indicated above, it may be formulated with water as liquid concentrated dye compositions, preferably with a dry substance content in the range of 10 to 70%, more preferably 20 to 50% by weight, referred to the weight of the composition.

The dyes of the invention advantageously contain at least one hyrosolubilizing group as stated above, in order to be readily hydrosoluble, and serve as hydrosoluble dyes, especially, if they contain at least one anionic group, they serve as anionic dyes; they are suitable for the dyeing of substrates dyeable with hydrosoluble dyes, especially anionic dyes. They may be used in the form as has been synthesized and, if necessary, purified or even be blended with conventional blending agents (in particular with inorganic salts, preferably sodium carbonate, sulphate or chloride, with non-electrolyte blending agents, preferably dextrine and/or urea and optionally—for the production of granular or liquid forms—with corresponding suitable additives). The dyes may be used in any conventional form, e.g. as powder, liquid compositions or granules; for the production of especially electrolyte-poor compositions, the dyes may be purified, e.g. by dialysis, before any blending with non-electrolyte blending agents.

The dyes of the invention may be of any hue, depending on the further components in particular A, Z, Me and/or Lg, principally ranging from red shades to yellow shades and to green shades (including also bluish red shades, orange shades, brown shades and olive shades); there may, however, also be produced dyes of other shades, in particular ranging from blue shades to gray and to black shades (including also violet shades).

Any substrate that is dyeable with hydrosoluble dyes, in particular with anionic dyes, is suitable as a substrate that may be dyed with the azo dyes resp. metal complexes of the invention; these include natural and regenerated cellulose, polyurethanes, basically modified high polymers (e.g. basically modified polypropylene), natural or synthetic polyamides or anodized aluminium, in particular, however, leather substrates. The substrate to be dyed may be in any conventional form, e.g. in the form of loose fibres, filaments, yarns, woven or knitted goods, non-woven webs, carpets, half-ready-made and ready-made soft goods and tanned leather or pelts. The dyes may be employed in any desired concentration up to the saturation of the substrate. The dyeing may be carried out by any conventional methods that are suitable for the substrate to be dyed, e.g. by exhaustion or impregnation methods (e.g. padding, spraying, foam application or application with a roller, or printing), preferably from aqueous medium; for synthetic substrates, the dye may optionally also be incorporated into the synthetic mass. Paper may be dyed in the pulp or after sheet formation.

The dyes of the invention are, however, mainly suitable for the dyeing of leather and pelts.

Any kinds of leather which are conventionally dyed from aqueous medium are suitable, particularly grain leather (e.g. nappa from sheep, goat or cow and box-leather from calf or cow), suede leather (e.g. velours from sheep, goat or calf and hunting leather), split velours (e.g. from cow or calf skin), bukskin and nubuk leather;further also wool-bearing skins and furs (e.g. fur-bearing suede leather). The leather may have been tanned by any conventional tanning method, in particular vegetable, mineral, synthetic or combined tanned (e.g. chrome tanned, zirconyl tanned, aluminium tanned or semi-chrome tanned). If desired, the leather may also be re-tanned; for re-tanning there may be used any tanning agent conventionally employed for re-tanning, e.g. mineral, vegetable or synthetic tanning agents [e.g. chromium, zirconyl or aluminium derivatives, quebracho, chestnut or mimosa extracts, aromatic syntans, polyurethanes, (co)polymers of (meth)acrylic acid compounds or melamine/, dicyanodiamide/ and/or urea/formaldehyde resins]. Thus leathers of very high to very low affinity for anionic dyes may be used.

The leathers may be of various thicknesses, thus, there may be used very thin leathers, such as book-binder's leather or glove-leather (nappa), leather of medium thickness, such as shoe upper leather, garment leather and leather for handbags, or also thick leathers, such as shoe-sole leather, furniture leather, leather for suitcases, for belts and for sport articles; hear-bearing leathers and furs may also be used. After tanning (in particular after a re-tanning) and before dyeing, the pH of the leather is advantageously set to values in the range of 4 to 8 (the leather is "neutralized"); depending on the kind of the leather, there may be chosen an optimum pH range, e.g. for grain leather pH values in the range of 4 to 6, for suede leather and split velours and for very thin leathers pH-values in the range of 4.5 to 8, for intermediately dried suede leathers and intermediately dried split velours the pH may range in the scope of 5 to 8. For the adjustment of the pH-value of the leather there may be employed conventional assistants; for tanned leather of acidic character the pH may be adjusted by addition of suitable bases, e.g. ammonia, ammonium bicarbonate or alkali metal salts of weak acids, e.g. sodium formate, sodium acetate, sodium bicarbonate, sodium carbonate or sodium sulphite, of which sodium formate and sodium bicarbonate are preferred. Sodium carbonate and sodium bicarbonate are usable in particular as second bases for the exact adjustment of the superficial pH-value of the leather. Mineral tanned leather may, if desired, also be masked, e.g. with alkali metal formate, oxalate or polyphosphate or e.g. with titanium/ potassium oxalate.

The dyeing may be carried out in a manner known per se suitably in an aqueous medium and under conventional temperature and pH conditions, in particular in the temperature range of 20° to 80° C., preferably 25° to 70° C., milder temperature conditions, in particular in the range of 25° to 40° C., being preferred for the achievement of deeper penetrations and for the dyeing of wool-bearing skins and furs. The pH-values of the dye-bath may, in general, range broadly, mainly from pH 8 to pH 3; in general the dyeing may be advantageously begun at higher pH-values and concluded at lower pH-values. Preferably the dyeing is carried out at pH-values $\geq 4$, in particular in the pH-range of 8 to 4, and for the conclusion of the dyeing procedure the pH-value is lowered (e.g. by addition of an acid conventional in the leather dyeing technique such as acetic acid or formic acid) preferably to values in the range between 4 and 3. The dye concentration may range broadly, if desired, up to the saturation degree of the substrate, e.g. up to 5%, referred to the wet weight of the substrate. The dyeing may be carried out in one or more stages, e.g. in two stages, optionally with insertion of charge reversal of the substrate by means of conventional cationic assistants.

The dyes of the invention may, if desired, be employed in combination with conventional dyeing assistants, mainly non-ionic or anionic products (in particular surfactants, preferably hydrophilic polysaccharide derivatives, polyoxyethylated alkylphenols or alcohols, lignosulphonates or sulpho group-containing aromatic compounds).

A fatting may, if desired, be carried out before and/or after the dyeing process, in particular also in the same liquor. For fatting after the dyeing process the fatting agent is advantageously added before the pH of the liquor is lowered, preferably to values between 3 and 4.

For the fatting (in particular fat-liquoring) step there may be used any conventional natural animal, vegetable or mineral fat, fat oil or wax, or chemically modified animal or vegetable fat or oil, which include in particular tallow, fish oils, neats-foot oil, olive oil, castor oil, rapeseed oil, cottonseed oil, sesame oil, corn oil and japanese tallow, and chemically modified products thereof (e.g. hydrolysis, transesterification, oxidation, hydrogenation or sulphonation products), bees-wax, chinese wax, carnauba wax, montan wax, wool fat, birch oil, mineral oils with boiling range within 300° and 370° C. (particularly the so-called "heavy alkylates"), soft paraffin, medium paraffin, vaseline and methyl esters of $C_{14-22}$-fatty acids; and synthetic leather fatting agents, including esters, in particular partial esters of polybasic acids (e.g. phosphoric acid) with optionally oxyethylated fatty alcohols. Of the above mentioned the methyl ester, the sulphonation products and the phosphoric acid partial esters are particularly preferred. By the term "sulphonation" for the fatting agents, there is meant generally the introduction of the sulpho group including also the formation of a sulphato group (="sulphating") and the introduction of a sulpho group by reaction with a sulphite or $SO_2$ (="sulphiting").

A conventional leather softener, in particular a cationic leather softener may, if desired, be applied in a final step, particularly if fatting has been carried out with a sulphonated fat-liquoring agent.

The treated substrate may then be further treated in conventional manner, e.g. washed or/and rinsed, drained, dried and cured.

According to the invention there may be obtained azo dyes resp. metal complex dyes that display, even with a relatively low number of hydrosolubilizing substituents in A and optionally B or/and optionally Lg, a high solubility in water, especially where anionic dyes are in alkali metal salt form; they are distinguished by their stability to electrolytes (in particular inorganic ions), specifically also to bases and acids, and are also distinguished, especially on leather, by their build-up and a high degree of insensitivity to variations of the affinity of the leather towards anionic dyes, very level dyeings of outstanding penetration and high colour-yield being obtainable. The dyeings particularly on leather, especially those obtained with metal complexes, have excellent fastness properties, for example wet-fastnesses, fastness to rubbing, light-fastness and stability to PVC migration. They are readily combinable with other dyes, in particular such with similar tinctorial behaviour. There may be obtained very level, intense, fine dyeings, grain side and flesh side being very evenly dyed, the shade of the dyeings obtained with a same dye on different kinds of leather being equal or very similar; in admixture with corresponding dyes with which the dyes of the invention are combinable, there may also be obtained very intense and regular dyeings of high yield and optimum fastnesses. By the choice of the substituents some of the properties of the dyes (e.g. solubility, shade, build-up, penetration, levelness etc.) may be varied accordingly.

In the following Examples parts and percentages are, if not otherwise indicated, by weight; parts by weight relate to parts by volume as grams to milliliters. The temperatures are indicated in degrees Celsius. In the Application Examples the respective dyes are used in blended form containing 30% of the respective dye and the blending agent being Glauber's salt (sodium sulphate), the other products employed in the Application Examples are commercially available products conventional in the treatment of leather.

EXAMPLE 1a (Process variant b)

23.4 parts of 2-amino-4-nitro-1-phenol-6-sulphonic acid are diazotized in conventional way with $NaNO_2$ in the presence of hydrochloric acid and coupled to 24.1 parts of 6-amino-2-sulphanilylamino-3H-pyrimidin-4-one at pH 9–9.5 and temperature 5°–10° C. When the coupling reaction is completed, the suspension is heated to 80° C. and 12 parts of sodium acetate and 27 parts of chrome alum ($Cr^{3+}$-content=10%) are added. The pH is adjusted to 4.5–5 with a 25% sodium hydroxide solution and the suspension is heated to 100° C. The end point of the chromation is determined by means of thin layer chromatography. When the chromation is completed, the obtained mixture is cooled with ice to 10° C. and acidified by addition of 50 parts of an aqueous 30% solution of hydrochloric acid. The obtained suspension of the 1:2-chromium complex of the monoazo compound is diazotized by dropwise addition of 22 parts by volume of an aqueous 30% sodium nitrite solution. When the diazotization reaction is completed the sodium nitrite in excess is destroyed by addition of 1 part of aminosulphonic acid. A solution of 14.4 parts of 2-naphthol in 50 parts of water and 15 parts of an aqueous 25% sodium hydroxide solution is then added, and the pH is adjusted to 10 by the addition of 50 parts of an aqueous 25% sodium hydroxide solution. The pH is maintained at 10 during one hour and then lowered to 5 by addition of 10 parts of an aqueous 30% hydrochloric acid solution. The formed chromium complex dye is salted out with sodium chloride, suction filtered, dried and milled. It corresponds in the form of the free acid to the formula

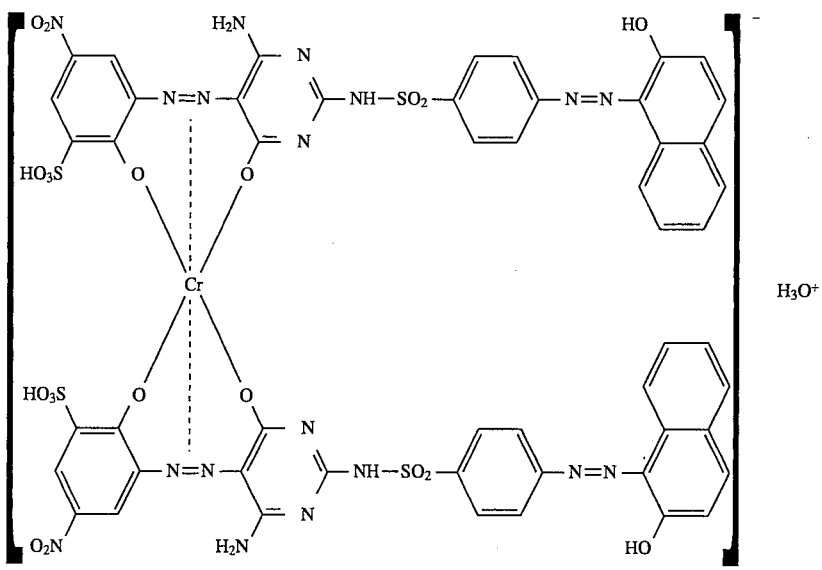

and is obtained in form of the sodium salt as a dark red powder that dyes leather in red shades.

The same dye as produced according to the above process variant b) can be produced according to process variant a) as follows:

(Process variant a)

23.4 parts of 2-amino-4-nitro-1-phenol-6-sulphonic acid are diazotized in conventional way with $NANO_2$ in the presence of hydrochloric acid and coupled to 24.1 parts of 6-amino-2-sulphanilylamino-3H-pyrimidin-4-one at pH 9–9.5 and temperature 5–10 C. When the coupling reaction is completed, 22 parts by volume of an aqueous 30% sodium nitrite solution are added, and the dyestuff solution is added dropwise into 50 parts of an aqueous 30% solution of hydrochloric acid that has been cooled with 100 parts of ice. When the diazotation reaction is completed the sodium nitrite in excess is destroyed by addition of 1 part of aminosulphonic acid. A solution of 14.4 parts of 2-naphthol in 50 parts of water and 15 parts of an aqueous 25% sodium hydroxide solution is then added, and the pH is adjusted to 10 by addition of 50 parts of an aqueous 25% sodium hydroxide solution. The pH is maintained at 10 during one hour. When the coupling reaction is completed, the suspension is heated to 80° C. and 12 parts of sodium acetate and 27 parts of chrom alum (Cr3+content=10%) are added. The pH is adjusted to 4.5–5 with a 25% sodium hydroxide solution and the suspension is heated to 100° C. The end point of the chromation is determined by means of thin layer chromatography. When the chromation is completed, the formed dye is salted out with sodium chloride, suction filtered, dried and milled. It corresponds in the form of the free acid to the formula indicated above in process variant b) of Example 1.

EXAMPLE 1b 23.4 parts of 2-amino-4-nitro-1-phenol-6-sulphonic acid are diazotized in conventional way with $NaNO_2$ in the presence of hydrochloric acid and coupled to 24.1 parts of 6-amino-2-sulphanilylamino-3H-pyrimidin-4-one at pH 9–9.5 and temperature 5°–10° C. When the coupling reaction is completed, the pH is adjusted to 11 with 5 parts of a 25% sodium hydroxide solution and the reaction mixture is heated to 60° C. Then 14 parts of cobalt sulphate heptahydrate, previously dissolved in 50 parts of water, are added over 10 minutes and, immediatly afterwards, 4 parts of hydrogen peroxide are slowly added. The pH is adjusted to 10 with 5 parts of a 2% sodium hydroxide solution. The end point of the cobaltation is determined by means of thin layer chromatography. When the cobaltation is completed, the obtained mixture is cooled with ice to 10° C. and acidified by addition of 50 parts of an aqueous 30% solution of hydrochloric acid. The obtained suspension of the 1:2-cobalt complex of the monoazo compound is diazotized by dropwise addition of 22 parts by volume of an aqueous 30% sodium nitrite solution. When the diazotization reaction is completed the sodium nitrite in excess is destroyed by addition of 1 part of aminosulphonic acid. A solution of 14.4 parts of 2-naphthol in 50 parts of water and 15 parts of an aqueous 25% sodium hydroxide solution are then added, and the pH is adjusted to 10 by the addition of 50 parts of an aqueous 25% sodium hydroxide solution. The pH is maintained at 10 during one hour and then lowered to 5 by addition of 10 parts of an aqueous 30% hydrochloric acid solution. The formed cobalt complex dye is salted out with sodium chloride, suction filtered, dried and milled. It corresponds in the form of the free acid to the formula

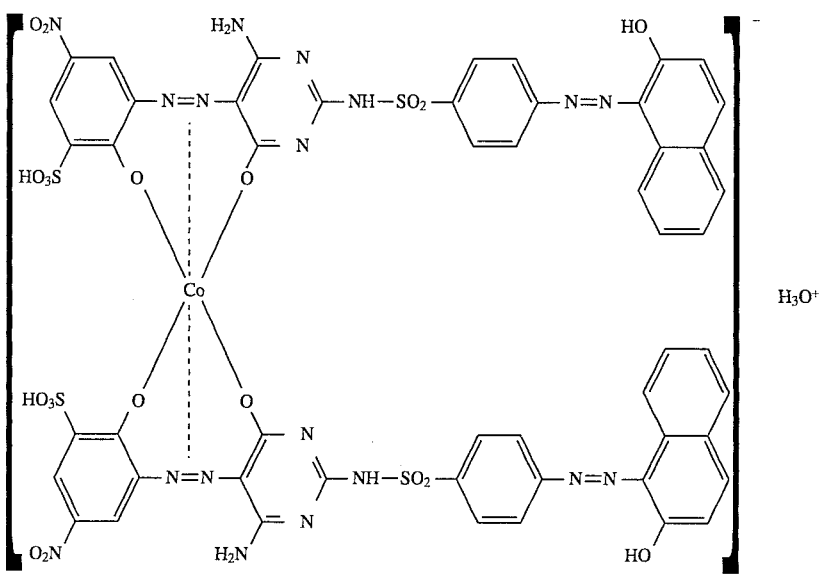

and is obtained in form of the sodium salt as a brown powder that dyes leather in orange-brown shades.

The same dye can also be obtained analogously as described in process variant a) of Example 1 by carrying out the cobaltation after formation of the disazo dye.

EXAMPLE 1c 23.4 parts of 2-amino-4-nitro-1-phenol-6-sulphonic acid are diazotized in conventional way with $NaNO_2$ in the presence of hydrochloric acid and coupled to 24.1 parts of 6-amino-2-sulphanilylamino-3H-pyrimidin-4-one at pH 9–9.5 and temperature 5°–10° C. When the coupling reaction is completed, the pH is adjusted to 5–5.5 with 5 parts of a 25% hydrochloric acid solution.

The suspension is heated to 70° C. and 20 parts of a 40% solution of iron trichloride are added, keeping the pH 4.5–5 with 20 parts of a 25% sodium hydroxide solution. The end point of the metallization is determined by means of thin layer chromatography. When the metallization is completed, the obtained mixture is cooled with ice to 10° C. and acidified by addition of 50 parts of an aqueous 30% solution of hydrochloric acid. The obtained suspension of the 1:2-iron complex of the monoazo compound is diazotized by dropwise addition of 22 parts by volume of an aqueous 30% sodium nitrite solution. When the diazotization reaction is completed the sodium nitrite in excess is destroyed by addition of 1 part of aminosulphonic acid. A solution of 14.4 parts of 2-naphthol in 50 parts of water and 15 parts of an aqueous 25% sodium hydroxide solution are then added, and the pH is adjusted to 10 by the addition of 50 parts of an aqueous 25% sodium hydroxide solution. The pH is maintained at 10 during one hour and then lowered to 5 by addition of 10 parts of an aqueous 30% hydrochloric acid solution. The formed iron complex dye is salted out with sodium chloride, suction filtered, dried and milled. It corresponds in the form of the free acid to the formula

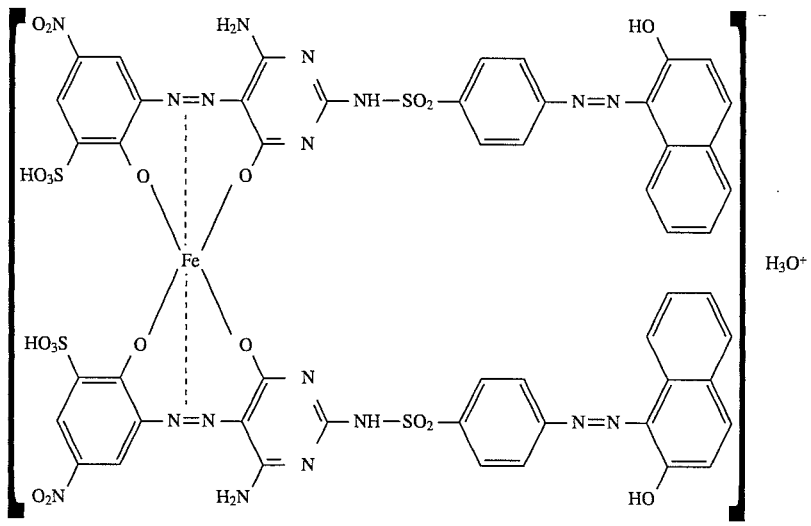

and is obtained in form of the sodium salt as a dark brown powder that dyes leather in brown shades.

The same dye can also be obtained analogously as described in process variant a) of Example 1a by carrying out the metallization after formation of the disazo dye.

EXAMPLES 2 to 57

The following tables contain further examples of disazodyes and their metal complexes, of the invention, that can be synthetized analogously as described in Example 1a, 1b and 1c, but using instead of 2-amino-1-hydroxy-4-nitrobenzene-6-sulphonic acid (diazo component Dk. 1 of the following list) equimolar amounts of the other amines (diazo components numbered as Dk. 2 to 19 in the following tables) set out in the following tables; the employed middle components are of formula (I') in which R signifies hydrogen, the amino group linked to the $-SO_2$-bound phenyl radical is in para-position to $-SO_2-$ and the substituents $X_1$ and $Y_1$ have the indicated significances; the complex-forming metals are chromium, cobalt and iron, as indicated. The shades of the dyeings obtained on leather with the respective 1:2 metal complexes is indicated under the relative headings indicating the complex-forming metal, the ones obtained with the non-metallized dyes are indicated under the heading "no Me".

The compound of formula (I') in which $X_1$ and $Y_1$ signify $-NH_2$, R signifies hydrogen and the primary amino group linked to the benzene ring is in para-position to $-SO_2-$ may be synthetized as follows:

23 parts of 4-amino-benzenesulphonylguanidine (="sulfaguanidine") are added to 100 parts of a 30% solution of sodium methylate in methanol. The mixture is heated to 50° C. and 15 parts of malononitrile are added slowly. Then the mixture is heated to reflux for 1 hour. Once the cyclization reaction is completed and after the addition of 100 parts of water, methanol is distilled off by increasing the temperature to 95° C. Finally the pH is decreased to 5 by addition of 22 parts of a 30% hydrochloric acid solution and the product is isolated by filtration at 80° C.

| Ex. no. | Dk. no. | $R_8$ | Amines of formula ($a_2$) $R_9$ | $X_1$ | $Y_1$ | Shade on leather chromium | cobalt | iron |
|---|---|---|---|---|---|---|---|---|
| 1 | 1 | $-SO_3H$ | $-NO_2$ | OH | $NH_2$ | red | orange | brown |
| 2 | 1 | $-SO_3H$ | $-NO_2$ | OH | OH | red | orange | brown |
| 3 | 1 | $-SO_3H$ | $-NO_2$ | $NH_2$ | $NH_2$ | red | orange | brown |
| 4 | 2 | $-NO_2$ | $-SO_3H$ | OH | $NH_2$ | red | orange | brown |
| 5 | 2 | $-NO_2$ | $-SO_3H$ | OH | OH | red | orange | brown |
| 6 | 2 | $-NO_2$ | $-SO_3H$ | $NH_2$ | $NH_2$ | red | orange | brown |
| 7 | 3 | H | $-SO_3H$ | OH | $NH_2$ | red | orange | brown |
| 8 | 3 | H | $-SO_3H$ | OH | OH | red | orange | brown |
| 9 | 3 | H | $-SO_3H$ | $NH_2$ | $NH_2$ | red | orange | brown |
| 10 | 4 | H | $-NO_2$ | OH | $NH_2$ | red | orange | brown |
| 11 | 4 | H | $-NO_2$ | OH | OH | red | orange | brown |
| 12 | 4 | H | $-NO_2$ | $NH_2$ | $NH_2$ | red | orange | brown |
| 13 | 5 | H | $-SO_2-NH_2$ | OH | $NH_2$ | red | orange | brown |
| 14 | 5 | H | $-SO_2-NH_2$ | OH | OH | red | orange | brown |
| 15 | 5 | H | $-SO_2-NH_2$ | $NH_2$ | $NH_2$ | red | orange | brown |
| 16 | 6 | H | $-SO_2-NH-\phenyl$ | OH | $NH_2$ | red | orange | brown |
| 17 | 6 | H | $-SO_2-NH-\phenyl$ | OH | OH | red | orange | brown |
| 18 | 6 | H | $-SO_2-NH-\phenyl$ | $NH_2$ | $NH_2$ | red | orange | brown |
| 19 | 7 | H | $-SO_2-NH-CH_3$ | OH | $NH_2$ | red | orange | brown |
| 20 | 7 | H | $-SO_2-NH-CH_3$ | OH | OH | red | orange | brown |
| 21 | 7 | H | $-SO_2-NH-CH_3$ | $NH_2$ | $NH_2$ | red | orange | brown |
| 22 | 8 | H | $-SO_2-NH-CH_2-CH_2-OH$ | OH | $NH_2$ | red | orange | brown |
| 23 | 8 | H | $-SO_2-NH-CH_2-CH_2-OH$ | OH | OH | red | orange | brown |
| 24 | 8 | H | $-SO_2-NH-CH_2-CH_2-OH$ | $NH_2$ | $NH_2$ | red | orange | brown |
| 25 | 9 | H | $-SO_2-NH-\phenyl(HOOC)$ | OH | $NH_2$ | red | orange | brown |

-continued

| 26 | 9 | H | —SO₂—NH—C₆H₄(HOOC) | | OH | OH | red | orange | brown |
|---|---|---|---|---|---|---|---|---|---|
| 27 | 9 | H | —SO₂—NH—C₆H₄(HOOC) | | NH₂ | NH₂ | red | orange | brown |
| 28 | 10 | H | Cl | | OH | NH₂ | red | orange | brown |
| 29 | 10 | H | Cl | | OH | OH | red | orange | brown |
| 30 | 10 | H | Cl | | NH₂ | NH₂ | red | orange | brown |
| 31 | 11 | H | —CH₃ | | OH | NH₂ | red | orange | brown |
| 32 | 11 | H | —CH₃ | | OH | OH | red | orange | brown |
| 33 | 11 | H | —CH₃ | | NH₂ | NH₂ | red | orange | brown |
| 34 | 12 | H | —SO₂—CH₃ | | OH | NH₂ | red | orange | brown |
| 35 | 12 | H | —SO₂—CH₃ | | OH | OH | red | orange | brown |
| 36 | 12 | H | —SO₂—CH₃ | | NH₂ | NH₂ | red | orange | brown |
| 37 | 13 | H | —NO₂ | | OH | NH₂ | red | orange | brown |
| 38 | 13 | H | —NO₂ | | OH | OH | red | orange | brown |
| 39 | 13 | H | —NO₂ | | NH₂ | NH₂ | red | orange | brown |

Amines of formula (a₃)

| Ex. no. | Dk. no. | $R_{10}$ | $X_1$ | $Y_1$ | Shade on leather chromium | cobalt | iron |
|---|---|---|---|---|---|---|---|
| 40 | 14 | —SO₃H | OH | NH₂ | red | orange | brown |
| 41 | 14 | —SO₃H | OH | OH | red | orange | brown |
| 42 | 14 | —SO₃H | NH₂ | NH₂ | red | orange | brown |
| 43 | 15 | —NO₂ | OH | NH₂ | red | orange | brown |
| 44 | 15 | —NO₂ | OH | OH | red | orange | brown |
| 45 | 15 | —NO₂ | NH₂ | NH₂ | red | orange | brown |
| 46 | 16 | —SO₂—NH₂ | OH | NH₂ | red | orange | brown |
| 47 | 16 | —SO₂—NH₂ | OH | OH | red | orange | brown |
| 48 | 16 | —SO₂—NH₂ | NH₂ | NH₂ | red | orange | brown |
| 49 | 17 | —SO₂—NH—CH₃ | OH | NH₂ | red | orange | brown |
| 50 | 17 | —SO₂—NH—CH₃ | OH | OH | red | orange | brown |
| 51 | 17 | —SO₂—NH—CH₃ | NH₂ | NH₂ | red | orange | brown |

Amines of formula

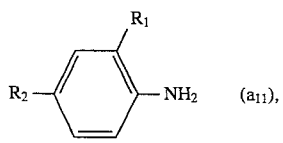

(a₁₁),

| Ex. no. | Dk. no. | $R_1$ | $R_2$ | $X_1$ | $Y_1$ | Shade on leather chromium | cobalt | iron | no Me |
|---|---|---|---|---|---|---|---|---|---|
| 52 | 18 | —COOH | H | OH | NH₂ | red | red | brown | orange |
| 53 | 18 | —COOH | H | OH | OH | red | red | brown | orange |
| 54 | 18 | —COOH | H | NH₂ | NH₂ | red | red | brown | orange |
| 55 | 19 | —COOH | —SO₃H | OH | NH₂ | red | red | brown | orange |
| 56 | 19 | —COOH | —SO₃H | OH | OH | red | red | brown | orange |
| 57 | 19 | —COOH | —SO₃H | NH₂ | NH₂ | red | red | brown | orange |

EXAMPLES 58 to 195

The following tables contain further examples of dyes of the invention, that can be synthetized analogously as described in Examples 1, 1bis and 1ter, but using instead of the coupling component 2-naphthol (coupling component Kk. 1 of the following list) equimolar amounts of the other coupling components (numbered as Kk. 2 to 46 in the following tables) set out in the following tables; the employed middle components are of formula (I') in which R signifies hydrogen, the amino group is in para-position and the substituents $X_1$ and $Y_1$ have the indicated significances; and the complex-forming metals are chromium, cobalt and iron, as indicated. The shades of the dyeings obtained on leather with the respective 1:2 metal complexes is indicated under the relative headings indicating the complex-forming metal.

Coupling components of formula

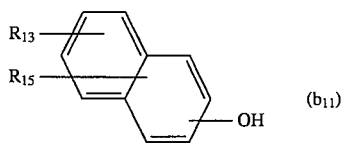

| Ex. no. | Kk. no. | Position of —OH | $R_{15}$ (position) | $R_{13}$ (position) | $X_1$ | $Y_1$ | Shade on leather chromium | cobalt | iron |
|---|---|---|---|---|---|---|---|---|---|
| 1 | 1 | 2 | H | H | OH | $NH_2$ | red | orange | brown |
| 58 | 1 | 2 | H | H | OH | OH | red | orange | brown |
| 59 | 1 | 2 | H | H | $NH_2$ | $NH_2$ | red | orange | brown |
| 60 | 2 | 2 | —COOH (3) | H | OH | $NH_2$ | red | orange | brown |
| 61 | 2 | 2 | —COOH (3) | H | OH | OH | red | orange | brown |
| 62 | 2 | 2 | —COOH (3) | H | $NH_2$ | $NH_2$ | red | orange | brown |
| 63 | 3 | 2 | —CO—$NH_2$ (3) | H | OH | $NH_2$ | red | orange | brown |
| 64 | 3 | 2 | —CO—$NH_2$ (3) | H | OH | OH | red | orange | brown |
| 65 | 3 | 2 | —CO—$NH_2$ (3) | H | $NH_2$ | $NH_2$ | red | orange | brown |
| 66 | 4 | 1 | H | H | OH | $NH_2$ | red | orange | brown |
| 67 | 4 | 1 | H | H | OH | OH | red | orange | brown |
| 68 | 4 | 1 | H | H | $NH_2$ | $NH_2$ | red | orange | brown |
| 69 | 5 | 2 | —$SO_3H$ (6) | H | OH | $NH_2$ | red | orange | brown |
| 70 | 5 | 2 | —$SO_3H$ (6) | H | OH | OH | red | orange | brown |
| 71 | 5 | 2 | —$SO_3H$ (6) | H | $NH_2$ | $NH_2$ | red | orange | brown |
| 72 | 6 | 1 | —$SO_3H$ (3) | —$NH_2$ (6) | OH | $NH_2$ | red | orange | brown |
| 73 | 6 | 1 | —$SO_3H$ (3) | —$NH_2$ (6) | OH | OH | red | orange | brown |
| 74 | 6 | 1 | —$SO_3H$ (3) | —$NH_2$ (6) | $NH_2$ | $NH_2$ | red | orange | brown |
| 75 | 7 | 1 | —$SO_3H$ (3) | —$NH_2$ (7) | OH | $NH_2$ | red | orange | brown |
| 76 | 7 | 1 | —$SO_3H$ (3) | —$NH_2$ (7) | OH | OH | red | orange | brown |
| 77 | 7 | 1 | —$SO_3H$ (3) | —$NH_2$ (7) | $NH_2$ | $NH_2$ | red | orange | brown |

Coupling components of formula ($b_2$) in which $R_{21}$ signifies H

| Ex. no. | Kk. no. | $R_{19}$ | $R_{20}$ (position) | $X_1$ | $Y_1$ | Shade on leather chromium | cobalt | iron |
|---|---|---|---|---|---|---|---|---|
| 78 | 8 | —OH | H | OH | $NH_2$ | orange | orange | brown |
| 79 | 8 | —OH | H | OH | OH | orange | orange | brown |
| 80 | 8 | —OH | H | $NH_2$ | $NH_2$ | orange | orange | brown |
| 81 | 9 | —OH | —$CH_3$ (4) | OH | $NH_2$ | orange | orange | brown |
| 82 | 9 | —OH | —$CH_3$ | OH | OH | orange | orange | brown |
| 83 | 9 | —OH | —$CH_3$ | $NH_2$ | $NH_2$ | orange | orange | brown |
| 84 | 10 | —OH | —$NH_2$ (3) | OH | $NH_2$ | orange | orange | brown |
| 85 | 10 | —OH | —$NH_2$ | OH | $OH_2$ | orange | orange | brown |
| 86 | 10 | —OH | —$NH_2$ | $NH_2$ | $NH_2$ | orange | orange | brown |
| 87 | 11 | —$NH_2$ | —$NH_2$ (3) | OH | $NH_2$ | orange | orange | brown |
| 88 | 11 | —$NH_2$ | —$NH_2$ | OH | OH | orange | orange | brown |
| 89 | 11 | —$NH_2$ | —$NH_2$ | $NH_2$ | $NH_2$ | orange | orange | brown |
| 90 | 12 | —$NH_2$ | —NH—CO—$CH_3$ (3) | OH | $NH_2$ | orange | orange | brown |
| 91 | 12 | —$NH_2$ | —NH—CO—$CH_3$ | OH | OH | orange | orange | brown |
| 92 | 12 | —$NH_2$ | —NH—CO—$CH_3$ | $NH_2$ | $NH_2$ | orange | orange | brown |
| 93 | 13 | —OH | —NH—CO—$CH_3$ (3) | OH | $NH_2$ | orange | orange | brown |
| 94 | 13 | —OH | —NH—CO—$CH_3$ | OH | OH | orange | orange | brown |
| 95 | 13 | —OH | —NH—CO—$CH_3$ | $NH_2$ | $NH_2$ | orange | orange | brown |
| 96 | 14 | —OH | —OH (3) | OH | $NH_2$ | orange | orange | brown |
| 97 | 14 | —OH | —OH | OH | OH | orange | orange | brown |
| 98 | 14 | —OH | —OH | $NH_2$ | $NH_2$ | orange | orange | brown |

Coupling components of formula ($b_3$) in which $R_{23}$ signifies —$CH_3$

| Ex. no. | Kk. no. | $R_{24}$ | $R_{22}$ | $X_1$ | $Y_1$ | Shade on leather chromium | cobalt | iron |
|---|---|---|---|---|---|---|---|---|
| 99 | 15 | =O | H | OH | $NH_2$ | orange | orange | brown |
| 100 | 15 | =O | H | OH | OH | orange | orange | brown |
| 101 | 15 | =O | H | $NH_2$ | $NH_2$ | orange | orange | brown |
| 102 | 16 | =O | phenyl | OH | $NH_2$ | orange | orange | brown |
| 103 | 16 | =O | phenyl | OH | OH | orange | orange | brown |
| 104 | 16 | =O | phenyl | $NH_2$ | $NH_2$ | orange | orange | brown |
| 105 | 17 | =NH | phenyl | OH | $NH_2$ | orange | orange | brown |
| 106 | 17 | =NH | phenyl | OH | OH | orange | orange | brown |
| 107 | 17 | =NH | phenyl | $NH_2$ | $NH_2$ | orange | orange | brown |

-continued

| | | | | | | | | | |
|---|---|---|---|---|---|---|---|---|---|
| 108 | 18 | =O | 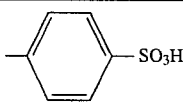 —⟨C₆H₄⟩—SO₃H | OH | NH₂ | orange | orange | brown | |
| 109 | 18 | =O | 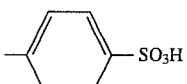 —⟨C₆H₄⟩—SO₃H | OH | OH | orange | orange | brown | |
| 110 | 18 | =O | 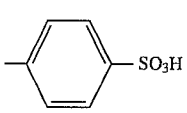 —⟨C₆H₄⟩—SO₃H | NH₂ | NH₂ | orange | orange | brown | |
| 111 | 19 | =O | 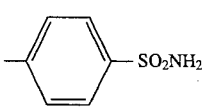 —⟨C₆H₄⟩—SO₂NH₂ | OH | NH₂ | orange | orange | brown | |
| 112 | 19 | =O | 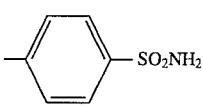 —⟨C₆H₄⟩—SO₂NH₂ | OH | OH | orange | orange | brown | |
| 113 | 19 | =O | 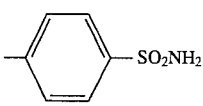 —⟨C₆H₄⟩—SO₂NH₂ | NH₂ | NH₂ | orange | orange | brown | |
| 114 | 20 | =O | 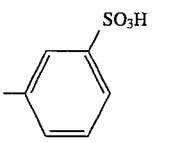 (SO₃H) | OH | NH₂ | orange | orange | brown | |
| 115 | 20 | =O | 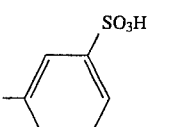 (SO₃H) | OH | OH | orange | orange | brown | |
| 116 | 20 | =O | 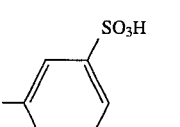 (SO₃H) | NH₂ | NH₂ | orange | orange | brown | |
| 117 | 21 | =O | 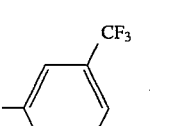 (CF₃) | OH | NH₂ | orange | orange | brown | |
| 118 | 21 | =O | 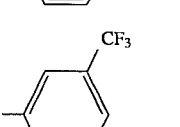 (CF₃) | OH | OH | orange | orange | brown | |
| 119 | 21 | =O | 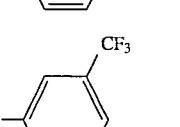 (CF₃) | NH₂ | NH₂ | orange | orange | brown | |

| | | Coupling components of formula (b₄) in which $R_{27}$ is methyl | | | | Shade on leather | | |
|---|---|---|---|---|---|---|---|---|
| Ex. no. | Kk. no. | $R_{25}$ | $R_{26}$ | $X_1$ | $Y_1$ | chromium | cobalt | iron |
| 120 | 22 | H | —CN | OH | NH₂ | orange | orange | brown |
| 121 | 22 | H | —CN | OH | OH | orange | orange | brown |
| 122 | 22 | H | —CN | NH₂ | NH₂ | orange | orange | brown |
| 123 | 23 | —(CH₂)₃—CH₃ | —CN | OH | NH₂ | orange | orange | brown |
| 124 | 23 | —(CH₂)₃—CH₃ | —CN | OH | OH | orange | orange | brown |
| 125 | 23 | —(CH₂)₃—CH₃ | —CN | NH₂ | NH₂ | orange | orange | brown |
| 126 | 24 | cyclohexyl | —CN | OH | NH₂ | orange | orange | brown |
| 127 | 24 | cyclohexyl | —CN | OH | OH | orange | orange | brown |
| 128 | 24 | cyclohexyl | —CN | NH₂ | NH₂ | orange | orange | brown |
| 129 | 25 | —CH₂—CH(C₂H₅)—(CH₂)₃—CH₃ | —CN | OH | NH₂ | orange | orange | brown |
| 130 | 25 | —CH₂—CH(C₂H₅)—(CH₂)₃—CH₃ | —CN | OH | OH | orange | orange | brown |
| 131 | 25 | —CH₂—CH(C₂H₅)—(CH₂)₃—CH₃ | —CN | NH₂ | NH₂ | orange | orange | brown |
| 132 | 26 | —CH₃ | —CN | OH | NH₂ | orange | orange | brown |
| 133 | 26 | —CH₃ | —CN | OH | OH | orange | orange | brown |
| 134 | 26 | —CH₃ | —CN | NH₂ | NH₂ | orange | orange | brown |
| 135 | 27 | —C₂H₅ | —CN | OH | NH₂ | orange | orange | brown |
| 136 | 27 | —C₂H₅ | —CN | OH | OH | orange | orange | brown |
| 137 | 27 | —C₂H₅ | —CN | NH₂ | NH₂ | orange | orange | brown |
| 138 | 28 | —C₂H₅ | —CONH₂ | OH | NH₂ | orange | orange | brown |
| 139 | 28 | —C₂H₅ | —CONH₂ | OH | OH | orange | orange | brown |
| 140 | 28 | —C₂H₅ | —CONH₂ | NH₂ | NH₂ | orange | orange | brown |
| 141 | 29 | H | H | OH | NH₂ | orange | orange | brown |
| 142 | 29 | H | H | OH | OH | orange | orange | brown |
| 143 | 29 | H | H | NH₂ | NH₂ | orange | orange | brown |
| 144 | 30 | —CH₂—CH₂—OH | —CO—NH₂ | OH | NH₂ | orange | orange | brown |
| 145 | 30 | —CH₂—CH₂—OH | —CO—NH₂ | OH | OH | orange | orange | brown |
| 146 | 30 | —CH₂—CH₂—OH | —CO—NH₂ | NH₂ | NH₂ | orange | orange | brown |
| 147 | 31 | —C₂H₅ | —SO₃H | OH | NH₂ | orange | orange | brown |
| 148 | 31 | —C₂H₅ | —SO₃H | OH | OH | orange | orange | brown |
| 149 | 31 | —C₂H₅ | —SO₃H | NH₂ | NH₂ | orange | orange | brown |
| 150 | 32 | 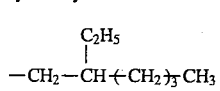 3-CF₃-phenyl | —CN | OH | NH₂ | orange | orange | brown |
| 151 | 32 | 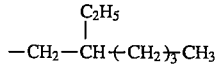 3-CF₃-phenyl | —CN | OH | OH | orange | orange | brown |
| 152 | 32 | 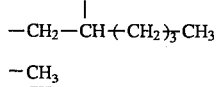 3-CF₃-phenyl | —CN | NH₂ | NH₂ | orange | orange | brown |
| 153 | 33 | H | 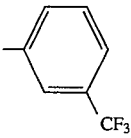 pyridinium | OH | NH₂ | orange | orange | brown |

| Ex. no. | Kk. no. | | | $X_1$ | $Y_1$ | Shade on leather chromium | cobalt | iron |
|---|---|---|---|---|---|---|---|---|
| 154 | 33 | H | —⁺N⟨pyridinyl⟩ | OH | OH | orange | orange | brown |
| 155 | 33 | H | —⁺N⟨pyridinyl⟩ | $NH_2$ | $NH_2$ | orange | orange | brown |
| 156 | 34 | H | —⁺N⟨methylpyridinyl⟩ | OH | $NH_2$ | orange | orange | brown |
| 157 | 34 | H | —⁺N⟨methylpyridinyl⟩ | OH | OH | orange | orange | brown |
| 158 | 34 | H | —⁺N⟨methylpyridinyl⟩ | $NH_2$ | $NH_2$ | orange | orange | brown |

Coupling components of formula ($b_5$) in which $R_{29}$ signifies —OH

| Ex. no. | Kk. no. | $R_{28}$ | $R_{30}$ | $X_1$ | $Y_1$ | Shade on leather chromium | cobalt | iron |
|---|---|---|---|---|---|---|---|---|
| 159 | 35 | —OH | —OH | OH | $NH_2$ | orange | orange | brown |
| 160 | 35 | —OH | —OH | OH | OH | orange | orange | brown |
| 161 | 35 | —OH | —OH | $NH_2$ | $NH_2$ | orange | orange | brown |
| 162 | 36 | —NH—CN | —OH | OH | $NH_2$ | orange | orange | brown |
| 163 | 36 | —NH—CN | —OH | OH | OH | orange | orange | brown |
| 164 | 36 | —NH—CN | —OH | $NH_2$ | $NH_2$ | orange | orange | brown |
| 165 | 37 | phenylamino | —OH | OH | $NH_2$ | orange | orange | brown |
| 166 | 37 | phenylamino | —OH | OH | OH | orange | orange | brown |
| 167 | 37 | phenylamino | —OH | $NH_2$ | $NH_2$ | orange | orange | brown |
| 168 | 38 | —$NH_2$ | —$NH_2$ | OH | $NH_2$ | orange | orange | brovn |
| 169 | 38 | —$NH_2$ | —$NH_2$ | OH | OH | orange | orange | brown |
| 170 | 38 | —$NH_2$ | —$NH_2$ | $NH_2$ | $NH_2$ | orange | orange | brown |
| 171 | 39 | —$NH_2$ | —OH | OH | $NH_2$ | orange | orange | brown |
| 172 | 39 | —$NH_2$ | —OH | OH | OH | orange | orange | brown |
| 173 | 39 | —$NH_2$ | —OH | $NH_2$ | $NH_2$ | orange | orange | brown |
| 174 | 40 | —SH | —OH | OH | $NH_2$ | orange | orange | brown |
| 175 | 40 | —SH | —OH | OH | OH | orange | orange | brown |
| 176 | 40 | —SH | —OH | $NH_2$ | $NH_2$ | orange | orange | brown |

EXAMPLE 177

Coupling component
41:8-hydroxyquinoline; $X_1$=OH, $Y_1$=$NH_2$,
Shade on leather:
1:2-Cr complex: orange;
1:2-Co complex: red;
1:2-Fe complex: brown.

EXAMPLE 178 coupling component
41:8-hydroxyquinoline; $X_1$=OH, $Y_1$=OH,
Shade on leather:
1:2-Cr complex: orange;
1:2-Co complex: red;
1:2-Fe complex: brown. cl Example 179 coupling component
41:8-hydroxyquinoline; $X_1$=$NH_2$, $Y_1$=$NH_2$,
Shade on leather:
1:2-Cr complex: orange;
1:2-Co complex: red;
1:2-Fe complex: brown.

Coupling components of formula

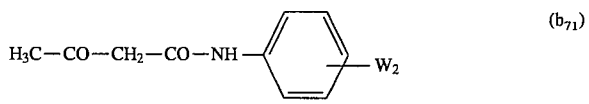

| Ex. no. | Kk. no. | $W_2$ | (position) | $X_1$ | $Y_1$ | Shade on leather chromium | cobalt | iron |
|---|---|---|---|---|---|---|---|---|
| 180 | 42 | H | | OH | $NH_2$ | orange | orange | brown |
| 181 | 42 | H | | OH | OH | orange | orange | brown |
| 182 | 42 | H | | $NH_2$ | $NH_2$ | orange | orange | brown |
| 183 | 43 | $-SO_3H$ | (4) | OH | $NH_2$ | orange | orange | brown |
| 184 | 43 | " | | OH | OH | orange | orange | brown |
| 185 | 43 | " | | $NH_2$ | $NH_2$ | orange | orange | brown |
| 186 | 44 | $-SO_2-NH_2$ | (4) | OH | $NH_2$ | orange | orange | brown |
| 187 | 44 | " | | OH | OH | orange | orange | brown |
| 188 | 44 | " | | $NH_2$ | $NH_2$ | orange | orange | brown |
| 189 | 45 | $-SO_3H$ | (3) | OH | $NH_2$ | orange | orange | brown |
| 190 | 45 | " | | OH | OH | orange | orange | brown |
| 192 | 45 | " | | $NH_2$ | $NH_2$ | orange | orange | brown |
| 193 | 46 | $-CF_3$ | (3) | OH | $NH_2$ | orange | orange | brown |
| 194 | 46 | " | | OH | OH | orange | orange | brown |
| 195 | 46 | " | | $NH_2$ | $NH_2$ | orange | orange | brown |

EXAMPLE 196a

The procedure described in Example 1a is repeated, with the difference that instead of Dk. 1 there is used the equivalent amount of Dk. 19, instead of 6-amino-2-sulphanilylamino-3H-pyrimidin-4-one there is used the equivalent amount of 2-sulphanilylamino-3H-pyrimidine-4,6-dione and instead of Kk. 1 there is used the equivalent amount of Kk. 42. The obtained chromium complex dyes leather in yellow shades; the non-metallized dye also dyes leather in yellow shades.

EXAMPLE 196b

The procedure described in Example 1b is repeated, with the difference that instead of Dk. 1 there is used the equivalent amount of Dk. 19, instead of 6-amino-2-sulphanilylamino-3H-pyrimidin-4-one there is used the equivalent amount of 2-sulphanilylamino-3H-pyrimidine-4,6-dione and instead of Kk. 1 there is used the equivalent amount of Kk. 42. The obtained cobalt complex dyes leather in brownish yellow shades.

EXAMPLE 197a

The procedure described in Example 196 is repeated, with the difference that instead of Kk. 42 there is used the equivalent amount of Kk. 15. The obtained chromium complex dyes leather in yellow shades; the non-metallized dye also dyes leather in yellow shades.

EXAMPLE 197b

The procedure described in Example 196b is repeated, with the difference that instead of Kk. 42 there is used the equivalent amount of Kk. 15. The obtained cobalt complex dyes leather in brownish yellow shades.

EXAMPLES 198 to 243

The procedure described in Examples 1a, 1b and 1c is repeated, with the difference that instead of Dk. 1 there is used the equivalent amount of 1-diazonium-2-naphthol-4-sulphonic acid (=Dk. 20), instead of 6-amino- 2-sulphanilylamino-3H-pyrimidin-4-one there is used the equivalent amount of 2-sulphanilylamino-3H-pyrimidine-4,6-dione and as Kk. there is used the equivalent amount of each of Kk. 1 to 46. The obtained chromium complexes obtained with Kk. 1 to 7 and 41 dye leather in bordeaux red shades. The obtained chromium complexes obtained with Kk. 8 to 40 and 42 to 46 dye leather in dark red shades. The obtained cobalt complexes obtained with Kk. 1 to 7 and 41 dye leather in bordeaux red shades. The obtained cobalt complexes obtained with Kk. 8 to 40 and 42 to 46 dye leather in dark red shades. The obtained iron complexes obtained with Kk. 1 to 7 and 41 dye leather in reddish brown shades. The obtained iron complexes obtained with Kk. 8 to 40 and 42 to 46 dye leather in dark brown shades.

EXAMPLES 244 to 289

The procedure described in Examples 198 to 243 is repeated, with the difference that instead of Dk. 20 there is used the equivalent amount of 1-diazonium-6-nitro-2-naphthol-4-sulphonic acid (=Dk. 21). The obtained chromium complexes obtained with Kk. 1 to 7 and 41 dye leather in bordeaux red shades. The obtained chromium complexes obtained with Kk. 8 to 40 and 42 to 46 dye leather in dark red shades. The obtained cobalt complexes obtained with Kk. 1 to 7 and 41 dye leather in bordeaux red shades. The obtained cobalt complexes obtained with Kk. 8 to 40 and 42 to 46 dye leather in dark red shades. The obtained iron complexes obtained with Kk. 1 to 7 and 41 dye leather in reddish brown shades. The obtained iron complexes obtained with Kk. 8 to 40 and 42 to 46 dye leather in dark brown shades.

EXAMPLE 290

The monoazo dyestuff obtained in the first step of Example 196 and the 1:1 Cr complex of the monoazo dye, which in the form of the free acid corresponds to the formula

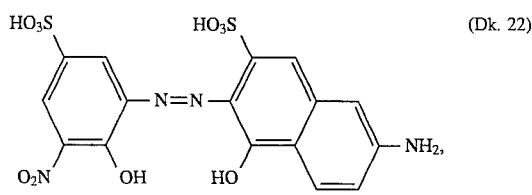

(Dk. 22)

obtained by coupling the diazotization product of 23.4 parts 6-nitro-2-amino-1-phenol-4-sulphonic acid (Dk. 2) to 23.9 parts of 1-hydroxy-6-aminonaphthalene-3-sulphonic acid (Kk. 6) under alkaline conditions, are placed together in a flask with 800 parts of water. The mixture is heated to 80° C. and the pH is adjusted to 8–8.5 with 40 parts by volume of a 5n solution of sodium hydroxide. Once the reaction is completed, the mixture is cooled to 10° C. with ice, acidified with 100 parts by volume of a 30% aqueous solution of hydrochloric acid and diazotized by the dropwise addition of 44 parts by volume of a 35% aqueous solution of sodium nitrite.

After two hours 35.4 parts of acetoacetanilide (=Kk. 42) suspended in 100 parts by volume of water are added, and the pH is adjusted to 10 with 70 parts by volume of a 25% aqueous solution of sodium hydroxide. After one hour the pH is adjusted to 5 with 10 parts by volume of a 30% aqueous solution of hydrochloric acid and the dye is salted out with sodium chloride. The obtained dye dyes leather in green shades. The asymmetrical 1:2-chromium complex corresponds in the form of the free acid to the formula

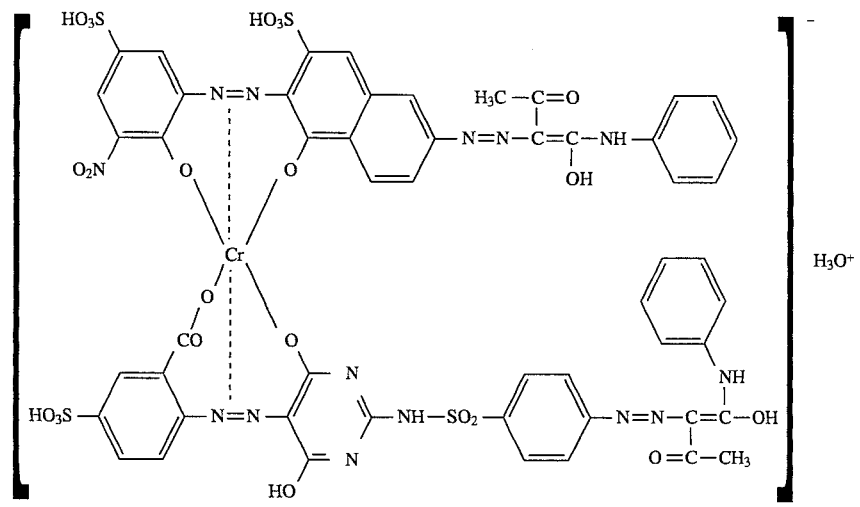

EXAMPLE 291

Example 290 is repeated with the difference that instead of Kk. 42 there is employed the equivalent amount of Kk. 15. The obtained dye dyes leather in green shades. The asymmetrical 1:2-chromium complex corresponds in the form of the free acid to the formula

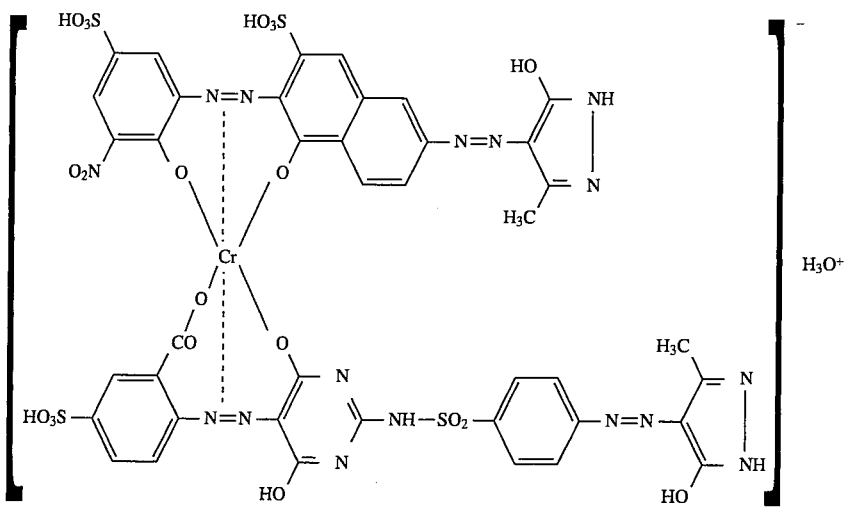
EXAMPLE 292
Example 290 is repeated with the difference that instead of Dk. 19 there is employed the equivalent amount of Dk. 18. The obtained dye dyes leather in green shades. The asymmetrical 1:2-chromium complex corresponds in the form of the free acid to the formula
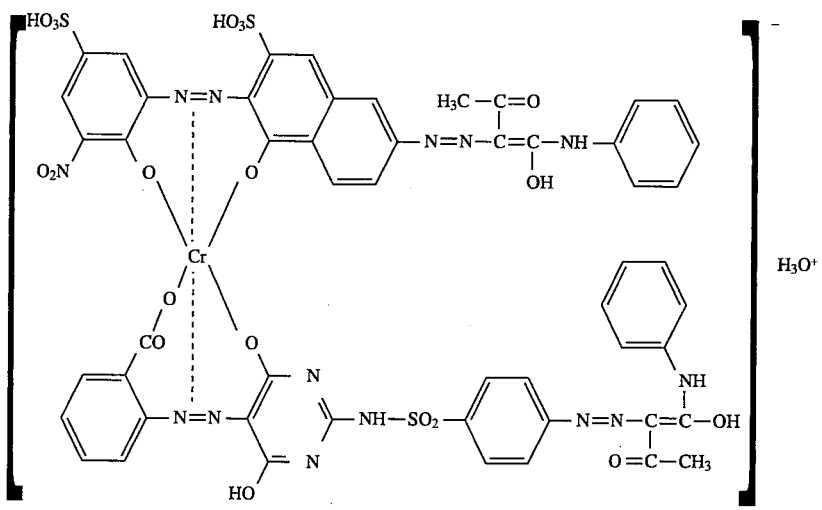

EXAMPLE 293

Example 292 is repeated with the difference that instead o#Kk. 42 there is employed the equivalent amount of Kk. 15. The obtained dye dyes leather in green shades. The asymmetrical 1:2-chromium complex corresponds in the form of the free acid to the formula

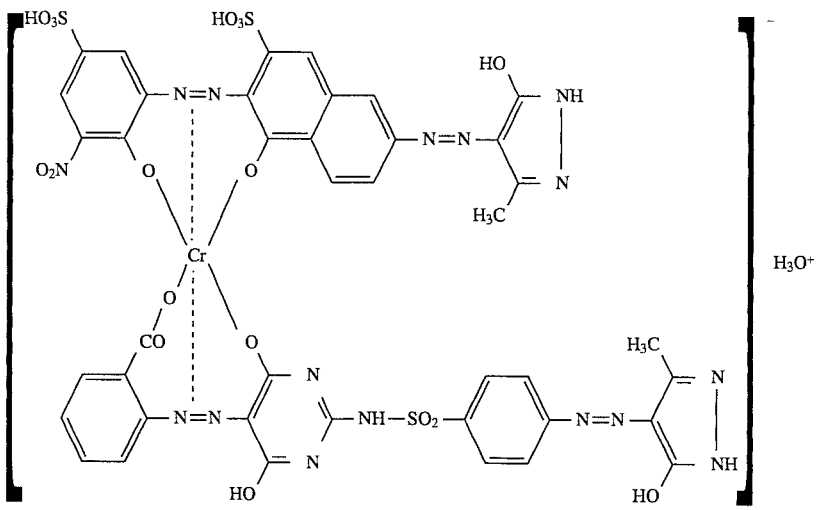

corresponds to the following formula:

EXAMPLE 294

25.7 parts of 2-amino-1-hydroxy-4-nitrobenzene-6-sulphonic acid (Dk. 1) are diazotized in a conventional way and coupled with 31.9 parts of 1-amino-8-hydroxynaphthalane-3,6-disulphonic acid at pH 9.5–10 and 5°–10° C. After 2 hours, the suspension is acidified with 50 parts of 30% hydrochloric acid, cooled with 50 parts of ice and diazotized with 20 parts by volume of an aqueous 30% solution of sodium nitrite. After 3 hours, the diazo suspension is added to a suspension of 28 parts of 2-sulphanilylamino-3H-pyrimidine- 4,6-dione in 100 parts of water, keeping the pH at 10. Once the coupling is finished, the disazo compound is precipitated by acidification to pH 1 and suction-filtered. The solid obtained is suspended in 300 parts of water, acidified with 50 parts of 30% hydrochloric acid and diazotized with 20 parts by volume of an aqueous 30% solution of sodium nitrite. After 3 hours 60 parts of an aqueous 25% suspension of 2-hydroxy-3-cyano- 4-methylpyrid-5-one (Kk. 22) are added, and the pH is increased to 10 with 60 parts of an aqueous 25% solution of sodium hydroxide. Finally, the dyestuff is salted out at pH 5. There is obtained an olive dyestuff, which, in the form of the free acid,

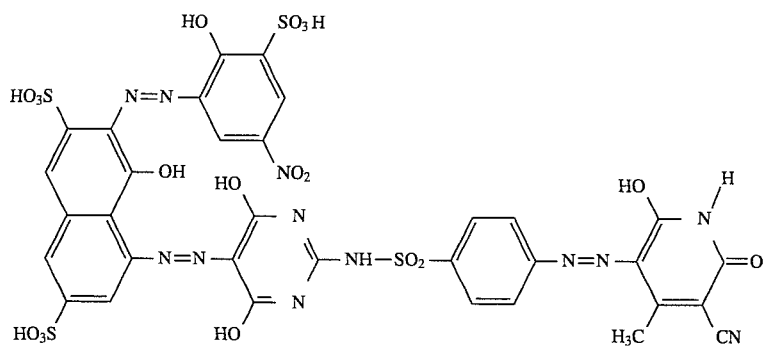

and dyes leather in olive shades.

EXAMPLE 295

Example 294 is repeated, with the difference that instead of Dk. 1 there is employed the same amount of Dk. 2. The obtained dye dyes leather in olive shades.

EXAMPLE 296

Example 294 is repeated, with the difference that instead of Kk. 22 there is employed the equivalent amount of Kk. 23. The obtained dye dyes leather in olive shades.

EXAMPLE 297

Example 296 is repeated, with the difference that instead of Dk. 1 there is employed the same amount of Dk. 2. The obtained dye dyes leather in olive shades.

EXAMPLE 298

Example 294 is repeated, with the difference that instead of Kk. 22 there is employed the equivalent amount of Kk. 33. The obtained dye dyes leather in olive shades.

EXAMPLE 299

Example 298 is repeated, with the difference that instead of Dk. 1 there is employed the same amount of Dk. 2. The obtained dye dyes leather in olive shades.

EXAMPLE 300

Example 294 is repeated, with the difference that instead of Kk. 22 there is employed the equivalent amount of Kk. 34. The obtained dye dyes leather in olive shades.

EXAMPLE 301

Example 300 is repeated, with the difference that instead of Dk. 1 there is employed the same amount of Dk. 2. The obtained dye dyes leather in olive shades.

EXAMPLE 302

14.4 parts of anthranilic acid (Dk. 18) are diazotized in conventional way with $NaNO_2$ in the presence of hydrochloric acid and coupled to 28.2 parts of 2-sulphanilylamino-3H-pyrimidin-4,6-dione at pH 9.5–10 and temperature 5°–10° C. After 1 hour 7.2 parts of sodium nitrite are added and the basic solution of the monoazo dye is added dropwise into a mixture of 50 parts of water and 50 parts of an aqueous 30% solution of hydrochloric acid. After 2 hours 25.4 parts of 3-methyl-1-phenyl-5-pyrazolone-4'-sulphonic acid are added and the pH is increased to 9 by the addition of an aqueous 25% sodium hydroxide solution. After 30 minutes the dye is precipitated by acidification with an aqueous 30% hydrochloric acid solution and suction-filtered. There is obtained a yellow dye, which in the form of the free acid corresponds to the formula

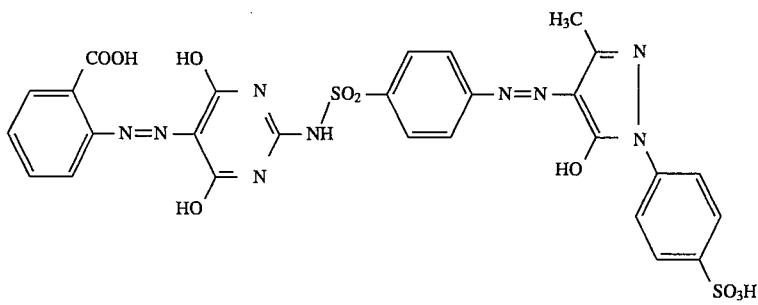

and dyes leather in yellow shades.

EXAMPLES 303 to 319

The following table contains further examples of disazodyes of the invention, that can be synthetized analogously as described in Example 302, but using instead of anthranilic acid (Dk no. 18) equimolar amounts of other amines of formula ($a_{12}$) below, indicated in the following table, or/and instead of 2-sulphanilylamino-3H-pyrimidin-4,6-dione equimolar amounts of the other middle components of formula (I') indicated in the following table in which R signifies hydrogen, the amino group linked to the —$SO_2$-bound phenyl radical is in para-position to —$SO_2$— and the substituents $X_1$ and $Y_1$ have the indicated significances, or/and instead of 3-methyl-1-phenyl-5-pyrazolone-4'-sulphonic acid equimolar amounts of the other coupling components indicated in the following table.

Amines of formula $$R_2 \underset{5\ 6}{\overset{3\ 2}{\underset{4}{\bigcirc}}}{}^{COOH}_{1} NH_2, \quad (a_{12})$$

| Ex. no. | Dk. no. | $R_2$ | (position) | $X_1$ | $Y_1$ | Kk. no. | Shade on leather |
|---|---|---|---|---|---|---|---|
| 302 | 18 | H | | OH | OH | 18 | yellow |
| 303 | 18 | H | | $NH_2$ | OH | 18 | yellow |
| 304 | 18 | H | | $NH_2$ | $NH_2$ | 18 | yellow |
| 305 | 19 | —$SO_3H$ | (4) | OH | OH | 16 | yellow |
| 306 | 19 | —$SO_3H$ | (4) | $NH_2$ | OH | 16 | yellow |
| 307 | 19 | —$SO_3H$ | (4) | $NH_2$ | $NH_2$ | 16 | yellow |
| 308 | 20 | —$SO_3H$ | (5) | OH | OH | 16 | yellow |
| 309 | 20 | —$SO_3H$ | (5) | $NH_2$ | OH | 16 | yellow |
| 310 | 20 | —$SO_3H$ | (5) | $NH_2$ | $NH_2$ | 16 | yellow |
| 311 | 21 | —$NO_2$ | (4) | OH | OH | 18 | yellow |
| 312 | 21 | —$NO_2$ | (4) | $NH_2$ | OH | 18 | yellow |
| 313 | 21 | —$NO_2$ | (4) | $NH_2$ | $NH_2$ | 18 | yellow |
| 314 | 22 | —$SO_2NH_2$ | (5) | OH | OH | 18 | yellow |
| 315 | 22 | —$SO_2NH_2$ | (5) | $NH_2$ | OH | 18 | yellow |
| 316 | 22 | —$SO_2NH_2$ | (5) | $NH_2$ | $NH_2$ | 18 | yellow |
| 317 | 23 | —$SO_2NHR_5'$ | (5) | OH | OH | 18 | yellow |
| 318 | 23 | —$SO_2NHR_5'$ | (5) | $NH_2$ | OH | 18 | yellow |
| 319 | 23 | —$SO_2NHR_5'$ | (5) | $NH_2$ | $NH_2$ | 18 | yellow | where $R_5'$ signifies a radical of formula

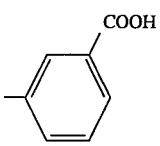

EXAMPLE 320

Example 302 is repeated, with the difference that instead of 4-amino-benzenesulphonylguanidine there is employed the equivalent amount of 1-amino-naphthalane-4-sulphonylguanidine to produce by reaction with malonic acid dimethylester the respective intermediate of formula

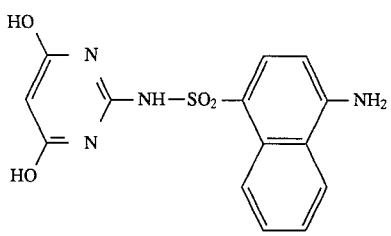

which is further reacted as indicated in Example 302 to give a disazodye, which in the form of the free acid corresponds to the formula

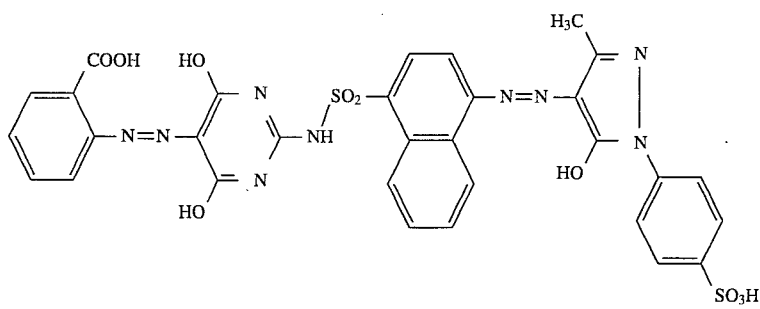

and dyes leather in yellow orange shades.

EXAMPLES 321 to 330

The following table contains further examples of dyes of the invention, that can be synthetized analogously as described in Examples 198 to 243, with the difference that instead of the coupling components Kk. 1 to 46 there are employed equimolar amounts of the coupling components of formula ($b_{12}$) below, numbered as Kk. 47 to 56 set out in the following table. The shades of the dyeings obtained on leather with the respective 1:2 metal complexes is indicated under the relative headings indicating the complex-forming metal.

Coupling components of formula ($b_{12}$)

| Ex. no. | Kk. no. | $R_{17}$ | position of $-NH-R_{17}$ | Shade on leather chromium | cobalt | iron |
|---|---|---|---|---|---|---|
| 321 | 47 | H | 6 | bordeaux | brown-bordeaux | brown |
| 322 | 48 | $-CH_3$ | 6 | bordeaux | brown-bordeaux | brown |
| 323 | 49 | $-CO-CH_3$ | 6 | bordeaux | brown-bordeaux | brown |
| 324 | 50 | phenyl | 6 | bordeaux | brown-bordeaux | brown |
| 325 | 51 | $-CO-$phenyl | 6 | bordeaux | brown-bordeaux | brown |
| 326 | 52 | H | 7 | bordeaux | brown-bordeaux | brown |
| 327 | 53 | $-CH_3$ | 7 | bordeaux | brown-bordeaux | brown |
| 328 | 54 | $-CO-CH_3$ | 7 | bordeaux | brown-bordeaux | brown |
| 329 | 55 | phenyl | 7 | bordeaux | brown-bordeaux | brown |

-continued

Coupling components of formula

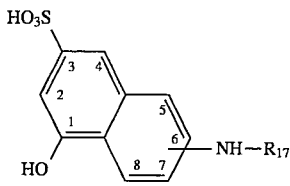
(b₁₂)

| Ex. no. | Kk. no. | R₁₇ | position of —NH—R₁₇ | Shade on leather chromium | cobalt | iron |
|---|---|---|---|---|---|---|
| 330 | 56 | —CO—C₆H₅ | 7 | bordeaux | brown-bordeaux | brown |

EXAMPLE 331

The procedure described in Examples 198 to 243 is repeated, with the difference that instead of Kk. 1 to 46 there is used the equivalent amount of 1-phenylamino-naphthalene-8-sulphonic acid (=Kk. 57). The obtained chromium complex dyes leather in bordeaux red shades. The obtained cobalt complex dyes leather in bordeaux red shades. The obtained iron complex dyes leather in brown shades.

Application Example A 100 parts of a wet blue bovine box side leather are neutralized in a dyeing drum with 250 parts of water and 0.8 parts of sodium bicarbonate at 35° C. during 45 minutes. The leather is then washed with 1000 parts of water at 25° C. After 5 minutes the leather is dyed at 50° C. with 250 parts of water and 0.8 parts of the chromium complex dye produced according to Example 1, previously dissolved in 80 parts of water of 50° C. After 20 minutes 4 parts of an 80% emulsion of a sulphited fish oil are added for fatting and fatting is continued for 45 minutes. Then the bath is acidified with 0.5 parts of an 85% formic acid solution and drumming is continued for 20 minutes. Finally the liquor is drained off and the leather is rinsed at 25° C. with 1000 parts of water. The leather is drained, dried and cured in conventional way. A leather dyed with a level red shade with outstanding fastnesses (in particular wet fastnesses, fastness to dry cleaning, fastness to light and PVC migration resistance) is obtained.

Application Example B 100 parts of an intermediately dried chrome-tanned suede split leather are wetted back with 800 parts of water at 50° C., 2 parts of 25% ammonia solution and 0.5 parts of the adduct of 10 moles of ethylene oxide to 1 mol of nonylphenol for 90 minutes; the bath is then drained off and 600 parts of water at 50° C., 1 part of a 25% ammonia solution and 1 part of a fat-liquoring agent (an emulsion of fatty acid esters) are added. After 10 minutes, 4 parts of the chromium complex dye produced according to Example 1, previously dissolved in 400 parts of water of 50° C., are added for pre-dyeing. After 60 minutes, 2 parts of an 85% formic acid are added and drumming is continued for 20 minutes. 2 parts of a 20% solution of the product obtained by quaternization with dimethylsulphate of the benzylation product of diethylenetriamine are then added and after 20 minutes 2 parts of the same dyestuff as used for pre-dyeing, previously dissolved in 200 parts of water of 50° C., are added. Drumming is continued for 40 minutes, then the bath is acidified with two additions of 1.5 parts of an 85% formic acid solution at an interval of 10 minutes between the two additions. After 10 minutes the bath is drained off and the leather is rinsed, drained, dried and cured as usual. There is obtained a leather dyed in a level red shade with outstanding fastnesses (in particular wet fastnesses, fastness to dry cleaning, fastness to light and PVC migration resistance).

Application Example C 100 parts of chrome-tanned bovine upholstery leather are wetted back with 800 parts of water, 2 parts of a 25% ammonia solution and 3 parts of the adduct of 10 moles of ethylene oxide to 1 mol of nonylphenol at 50° C. during 90 minutes. The bath is then drained off and the leather is treated for 15 minutes with 400 parts of water at 40° C., 1.5 parts of a 25% ammonia solution, 2 parts of a fat-liquoring agent (an emulsion of fatty acid esters) and 1 part of a phenolic syntan (condensation product of phenol and sulphuric acid). 6 parts of the chromium complex dye obtained in Example 1, previously dissolved in 600 parts of water of 50° C., are added and drumming is continued for 60 minutes. The bath is then acidified with two subsequent additions of 1.5 parts of an 85% formic acid solution, at an interval of 10 minutes. After 10 minutes the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example D 100 parts of chrome tanned bovine upholstery leather is wetted back with 800 parts of water, 2 parts of a 25% ammonia solution and 3 parts of the adduct of 10 moles of ethylene oxide to 1 mol of nonylphenol at 50° C. during 90 minutes. The liquor is then drained off and the leather is treated for 15 minutes with 400 parts of water at 40° C., 1.5 parts of a 25% ammonia solution, 2 parts of a fat-liquoring agent (an emulsion of fatty acid esters) and 1 part of a phenolic syntan (condensation product of phenol and sulphuric acid). The leather is then pre-dyed with 4 parts of the chromium complex dye obtained in Example 1, previously dissolved in 400 parts of water of 50° C. After 60 minutes, the bath is acidified with 1 part of an 85% formic acid solution and, after 10 minutes, 2 parts of a 20% solution of the product obtained by quaternization with dimethylsulphate of the benzylation product of diethylenetriamine are added. The bath is drained off after 20 minutes and the leather is dyed at 50° C. with 400 parts of water and 2 parts of the same dyestuff as used before for pre-dyeing, previously dissolved in 200 parts of water of 50° C., for 40 minutes. The bath is then acidified with 1 part of an 85% formic acid solution and, after 20 minutes, the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example E 100 parts of low affinity chrome/vegetable tanned bovine leather is wetted back at 50° C. with 1000 parts of water and 0.2 parts of the adduct of 10 moles of ethylene oxide to 1 mole of nonylphenol during 90 minutes. The bath is then drained off and the leather is dyed at 50° C. with 1000 parts of water and 4 parts of the chrome complex dye obtained in Example 1, previously dissolved in 400 parts of water of 50° C. After 1 hour, the bath is acidified with 2 parts of an 85% formic acid solution, and, after 20 minutes, the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example F 100 parts of semichrome sheep leather are wetted back at 45° C. with 1000 parts of water and 0.5 parts of an amphoteric masking agent (a sulpho group containing fatty acid aminoamide) for 1 hour. The leather is pre-dyed with 800 parts of water of 50° C. and 6 parts of the chromium complex dye obtained in Example 1, previously dissolved in 600 parts of water of 50° C. Drumming is continued until the dye has penetrated inside the leather. The bath is then acidified with 1.5 parts of an 85% formic acid solution and, after 20 minutes, 2 parts of a 20% solution of the product obtained by quaternization with dimethylsulphate of the benzylation product of diethylenetriamine are added. After 20 minutes the leather is dyed with 6 parts of the same dye as used for pre-dyeing, previously dissolved in 600 parts of water of 50° C., for 40 minutes. The bath is then acidified with 2 parts of an 85% formic acid solution and after 30 minutes the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example G 100 parts of chrome tanned crust bovine leather for upholstery are wetted back at 35° C. with 300 parts of water and 0.5 parts of an amphoteric masking agent (a sulpho group containing fatty acid aminoamide) for 20 minutes. The bath is drained off an the leather is retanned at 35° C. with 150 parts of water, 1 part of a phenolic syntan (65% solution of the condensation product of phenol and sulphuric acid) and 3 parts of a 40% solution of dimethyloldihydroxyethylene urea. After 30 minutes 1.5 parts of sodium formate are added and, after 15 minutes 5 parts of a polypeptide-based retanning agent are added. Drumming is continued for 30 minutes and then the pH of the bath is set to 6 by addition of 1.5 parts of sodium bicarbonate. After 30 minutes the leather is washed for 10 minutes with 300 parts of water at 40° C. Then 150 parts of water at 45° C., 1 part of a fat-liquoring agent (an emulsion of fatty acid esters), 1 part of a 25% ammonia solution and 0.5 parts of a phenolic syntan (condensation product of phenol and sulphuric acid) are added. After 15 minutes the leather is dyed with 3 parts of the chromium complex dye obtained in Example 1, previously dissolved in 300 parts of water of 50° C., during 90 minutes, i.e. until the dye has fully penetrated. 2 parts of an emulsion of fatty acid esters, 3 parts of a mixture of an esterified synthetic fatty alcohol and a phosphoric acid partial ester of an ethoxylated fatty alcohol and 6 parts of an emulsion of a sulphited fish-oil are added for fat-liquoring and, after 60 minutes, 2 parts of a hydrosoluble melamine-formaldehyde condensate are added for fixation. Drumming is continued for 20 minutes and then the bath is acidified with two additions of 0.75 parts of an 85% formic acid solution diluted with water 1:20 v/v, with an interval of 10 minutes between the two additions. After 10 minutes the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example H 100 parts of sheep nappa are washed 40° C. with 200 parts of water and 0.5 parts of an amphoteric masking agent (a sulpho group containing fatty acid aminoamide) for 20 minutes. The bath is drained off, 200 parts of water at 35° C. and 1.2 parts of sodium formate are added and drumming is continued for 15 minutes. 4 parts of a polypeptide-based retanning agent are then added and after 30 minutes 0.6 parts of sodium carbonate are added to adjust the pH of the bath to 5.8–6.0. After 40 minutes 4 parts of polyacrylic-acid-based retanning agent are added and drumming is continued for 30 minutes; 2 parts of a water-soluble urea/formaldehyde condensate are then added and after 30 minutes the bath is drained off. Then 150 parts of water at 40° C., 1 part of a 25% ammonia solution and 2 parts of a fat-liquoring agent (an emulsion of fatty acid esters) are added. After 10 minutes the leather is dyed with 3 parts of the chromium complex dye obtained in Example 1, previously dissolved in 300 parts of water of 50° C., during 90 minutes. 2 parts of an emulsion of fatty acid esters, 6 parts of an emulsion of a sulphited fish-oil and 3 parts of an aqueous emulsion of fatty alcohol phosphoric acid partial esters are added for fat-liquoring. Drumming is continued for 60 minutes and then the bath is acidified with 1.5 parts of an 85% formic acid solution. After 30 minutes the bath is drained off and the leather is rinsed, drained, dried and cured as conventional. There is obtained a leather dyed in a level red shade with outstanding fastnesses (in particular wet fastnesses, fastness to dry cleaning, fastness to light and PVC migration resistance).

Application Example I

Application Example H is repeated, with the difference that after fat-liquoring and before the conclusive formic acid addition the bath is drained off, 200 parts of water at 50° C. and 2 parts of a hydrosoluble polymeric reaction product of epichlorohydrin and dimethylamine are added, drumming is continued for 30 minutes, thereafter 0.5 parts of 2-fatty alkyl imidazoline are added and drumming is continued for further 20 minutes. The bath is then drained off and the leather is rinsed, drained, dried and cured as conventional. There is obtained a leather dyed in a level red shade with outstanding fastnesses (in particular wet fastnesses, fastness to dry cleaning, fastness to light and PVC migration resistance).

Analogously as the red dye according to Example 1, the dyes of each of Examples 1bis to 331 are used in each of the above Application Examples A to I, by which there are also obtained dyeings of corresponding shades, depths and fastnesses.

The following Table contains further Application Examples (Ap. Ex. J to U) in which Application Examples C, D or G (as indicated) are repeated, with the difference that in place of the red dye of Example 1 there is employed the same amount of a dye mixture of the red 1:2 chromium complex dye of Example 2, which in the following table is indicated as "Red Ex. 2 Cr", and another dye identified by its "Colour Index" denomination, the two dyes of the mixture being employed in the weight ratio of 2 parts of Dye 1 to 1 part of Dye 2.

TABLE

| Ap. Ex. | Dye 1 | Dye 2 | dyeing as in Ap. Ex. | shade on leather |
|---|---|---|---|---|
| J | Red Ex. 2 Cr | C.I. Acid Yellow 243 | C | orange |
| K | C.I. Acid Yellow 243 | Red Ex. 2 Cr | C | yellowish orange |
| L | Red Ex. 2 Cr | C.I. Acid Black 233 | C | reddish brown |
| M | C.I. Acid Black 233 | Red Ex. 2 Cr | C | reddish dark brown |
| N | Red Ex. 2 Cr | C.I. Acid Yellow 243 | D | orange |
| O | C.I. Acid Yellow 243 | Red Ex. 2 Cr | D | yellowish orange |
| P | Red Ex. 2 Cr | C.I. Acid Black 233 | D | reddish brown |
| Q | C.I. Acid Black 233 | Red Ex. 2 Cr | D | reddish dark brown |
| R | Red Ex. 2 Cr | C.I. Acid Yellow 243 | G | orange |
| S | C.I. Acid Yellow 243 | Red Ex. 2 Cr | G | yellowish orange |
| T | Red Ex. 2 Cr | C.I. Acid Brown 432 | G | brownish red |
| U | C.I. Acid Brown 432 | Red Ex. 2 Cr | G | reddish brown |

Analogously as the red dye of Example 2 Cr the dyes of each of Examples 1a, 1b and 1c, 2 Co, 2 Fe and 3 to 331 are used in each of the above Application Examples J to U, by which there are also obtained dyeings of corresponding mixed shade, depths and fastnesses.

We claim:

1. A compound of formula

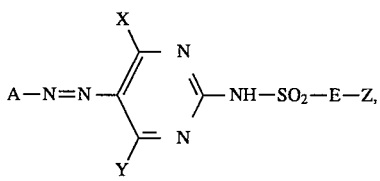

wherein
   A signifies the radical of a diazo component,
   X signifies $X_1$ or X',
   Y signifies $Y_1$ or Y',
   X' signifies $C_{1-4}$-alkoxy, a mono- or di-($C_{1-4}$-alkyl)-amino group, an acylamino group or a carboxymethylamino group,
   Y' signifies $C_{1-4}$-alkoxy, a mono- or di-($C_{1-4}$-alkyl)-amino group, an acylamino group or a carboxymethylamino group,
   Z signifies a primary amino group or $Z_1$,
   $Z_1$ signifies hydroxy, $C_{1-4}$-alkoxy, a mono- or di-($C_{1-4}$-alkyl)-amino group, an acylamino group, a carboxymethylamino group or a group —N=N—B,
   B signifies the radical of a coupling component
   E signifies an aromatic bivalent radical,
   $X_1$ signifies hydroxy or a primary amino group and
   $Y_1$ signifies hydroxy or a primary amino group,
or a mixture of compounds of formula (II).

2. A compound according to claim 1 of formula

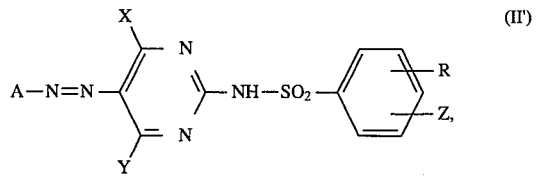

wherein R signifies hydrogen or methyl, or a mixture of compounds of formula (II').

3. A compound of formula (II) according to claim 1, which is a metallizable compound
   wherein
   A signifies the radical of a diazo component HO—(CO)$_n$—A$_1$—NH$_2$, in which the substituent —(CO)$_n$—OH is in ortho position to the diazotizable amino group,
   —A$_2$— is an ortho-bivalent radical and n signifies 0 or 1,
   or its modified derivative,
   X signifies $X_1$,
   and
   Z is in position meta or para to —SO$_2$—, and corresponding to the formula

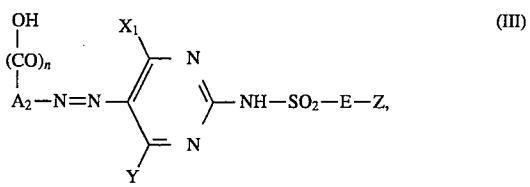

wherein $A_2$ is an ortho-bivalent radical $A_1$ or its modified derivative.

4. A compound according to claim 3 corresponding to the formula

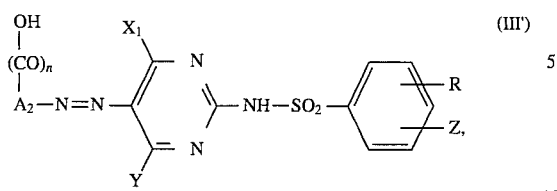

wherein R signifies hydrogen or methyl, or a mixture of two or more thereof.

5. A compound or mixture according to claim 1, wherein

A is the radical of a diazo component of the benzene or/and naphthalene series containing 1 to 4 aromatic rings and which, if it contains 2 to 4 aromatic rings, may contain a heteroatomic bridge between two aromatic rings, Z is a group —N=N—B, and B is the radical of a coupling component of the benzene, naphthalene, heterocyclic or open-chain methylene-active series.

6. A compound or mixture according to claim 3, wherein

—$A_2$—$(CO)_n$—OH is the radical of a diazo component of the benzene or/and naphthalene series containing 1 to 4 aromatic rings and which, if it contains 2 to 4 aromatic rings, may contain a heteroatomic bridge between two aromatic rings, Z is a group —N=N—B, and B is the radical of a coupling component of the benzene, naphthalene, heterocyclic or open-chain methylene-active series.

7. A process for the dyeing of a substrate dyeable with anionic dyes, wherein said substrate is dyed with an azodye or a mixture thereof according to claim 1.

8. A process for the dyeing of a substrate dyeable with anionic dyes, wherein said substrate is dyed with a mixture of an azo dye or a mixture thereof according to claim 1 and a metal complex of a metallizable azo dye of formula

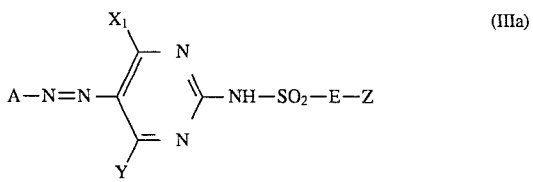

wherein

A signifies the radical of a diazo component HO—$(CO)_n$—$A_1$—$NH_2$, in which the substituent —$(CO)_n$—OH is in ortho position to the diazotizable amine group;

n signifies 0 or 1;

—$A_1$— signifies an ortho-bivalent radical;

$X_1$ signifies hydroxy or a primary amino group;

Y signifies $Y_1$ or Y';

$Y_1$ signifies hydroxy or a primary amino group;

Y' signifies $C_{1-4}$-alkoxy, a mono- or di-($C_{1-4}$-alkyl)-amino group, an acylamino group or a carboxymethylamino group;

E signifies an aromatic bivalent radical;

Z signifies a primary amino group, or $Z_1$ and is in a position meta or para to $SO_2$;

$Z_1$ signifies hydroxy, $C_{1-4}$-alkoxy, a mono-or di($C_{1-4}$-alkyl)-amino group, an acylamino group or a carboxymethylamino group or a group —N=N—B; and B signifies a radical of a coupling component or a mixture thereof.

9. A process according to claim 7 wherein said substrate is selected from the group consisting of leather and pelts.

10. A process according to claim 8 wherein said substrate is selected from the group consisting of leather and pelts.

* * * * *

UNITED STATES PATENT AND TRADEMARK OFFICE
CERTIFICATE OF CORRECTION

PATENT NO.  : 5,554,736
DATED       : September 10, 1996
INVENTOR(S) : JORDI BERENGUER BARRA
              JOSE ROCAS SOROLLA It is certified that error appears in the above-indentified patent and that said Letters Patent is hereby corrected as shown below:

On the title page, item [76], Inventors:

JORDI BERENGUER BARRA
   JOSE ROCAS SOROLLA

Signed and Sealed this

Twenty-fifth Day of February, 1997

Attest:

BRUCE LEHMAN

*Attesting Officer*  *Commissioner of Patents and Trademarks*